(12) United States Patent
Rack et al.

(10) Patent No.: US 8,853,410 B2
(45) Date of Patent: Oct. 7, 2014

(54) PROCESS FOR PREPARING SUBSTITUTED ISOXAZOLINE COMPOUNDS AND THEIR PRECURSORS

(75) Inventors: Michael Rack, Eppelheim (DE);
Karsten Koerber, Eppelheim (DE);
Florian Kaiser, Mannheim (DE)

(73) Assignee: BASF SE, Ludwigshafen (DE)

( * ) Notice: Subject to any disclaimer, the term of this patent is extended or adjusted under 35 U.S.C. 154(b) by 59 days.

(21) Appl. No.: 13/266,265

(22) PCT Filed: Apr. 29, 2010

(86) PCT No.: PCT/EP2010/055773
§ 371 (c)(1),
(2), (4) Date: Oct. 26, 2011

(87) PCT Pub. No.: WO2010/125130
PCT Pub. Date: Nov. 4, 2010

(65) Prior Publication Data
US 2012/0059171 A1 Mar. 8, 2012

(30) Foreign Application Priority Data
Apr. 30, 2009 (EP) .................... 09159246

(51) Int. Cl.
C07D 413/12 (2006.01)
C07D 413/04 (2006.01)
(52) U.S. Cl.
CPC .................. *C07D 413/04* (2013.01)
USPC ...................... 546/272.1; 548/240
(58) Field of Classification Search
USPC ...................... 546/272.1; 548/240
See application file for complete search history.

(56) References Cited

U.S. PATENT DOCUMENTS

| 2007/0066617 A1 | 3/2007 | Mita et al. |
| 2009/0023923 A1 | 1/2009 | Mizukoshi et al. |
| 2010/0137612 A1 | 6/2010 | Yaosaka et al. |
| 2010/0144797 A1 | 6/2010 | Mita et al. |
| 2010/0174094 A1 | 7/2010 | Zierke et al. |
| 2011/0144349 A1 | 6/2011 | Kousaka et al. |
| 2011/0172414 A1 | 7/2011 | Mita et al. |
| 2011/0251398 A1 | 10/2011 | Mita et al. |

FOREIGN PATENT DOCUMENTS

| EP | 1 932 836 | 6/2008 |
| JP | 2007/016017 | 1/2007 |
| JP | 2007/106756 | 4/2007 |
| JP | 2008/133242 | 6/2008 |
| JP | 2008/156347 | 7/2008 |
| JP | 2008/239611 | 10/2008 |
| WO | WO 2005/085216 | 9/2005 |
| WO | WO 2007/026965 | 3/2007 |
| WO | WO 2007/070606 | 6/2007 |
| WO | WO 2007/074789 | 7/2007 |
| WO | WO 2007/075459 | 7/2007 |
| WO | WO 2007/079162 | 7/2007 |
| WO | WO 2007/105814 | 9/2007 |
| WO | WO 2007/125984 | 11/2007 |
| WO | WO 2008/012027 | 1/2008 |
| WO | WO 2008/019760 | 2/2008 |
| WO | WO 2008/108448 | 9/2008 |
| WO | WO 2008/122375 | 10/2008 |
| WO | WO 2008/130651 | 10/2008 |
| WO | WO 2008/145740 | 12/2008 |

(Continued)

OTHER PUBLICATIONS

Dorwald, Side Reactions in Organic Synthesis, 2005, Wiley: VCH Weinheim Preface, pp. 1-15 & Chapter 8, pp. 279-308.*

(Continued)

*Primary Examiner* — Patricia L Morris
(74) *Attorney, Agent, or Firm* — Brinks Gilson & Lione

(57) ABSTRACT

The present invention relates to a new method of preparing halogenated styrene compounds of formula (VIII)

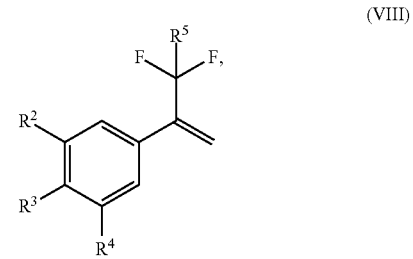

(VIII)

which are precursors in the process of synthesis of substituted isoxazoline compounds of formula (I)

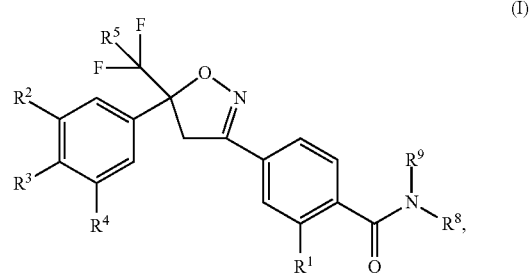

(I)

wherein $R^1$ to $R^5$, $R^8$ and $R^9$ are described as in the description.

The present invention relates further to the synthesis of compounds of formula (I) starting from acetophenones. The desired styrenes of formula are prepared from the appropriate substituted acetophenone. Asides bromo anilines react with formoxime. Obtained oximes undergo a cycloaddition with the styrenes and give isoxazolines. Compounds of formula (I) can then be prepared in a palladium catalyzed carbonylative amination reaction of the isoxazolines.

24 Claims, No Drawings

(56) References Cited

FOREIGN PATENT DOCUMENTS

| WO | WO 2008/150393 | 12/2008 |
|---|---|---|
| WO | WO 2008/154528 | 12/2008 |
| WO | WO 2009/001942 | 12/2008 |
| WO | WO 2009/002809 | 12/2008 |
| WO | WO 2009/003075 | 12/2008 |
| WO | WO 2009/024541 | 2/2009 |
| WO | WO 2009/049846 | 4/2009 |
| WO | WO 2009/063910 | 5/2009 |
| WO | WO 2009/126668 | 10/2009 |
| WO | WO 2009/142569 | 11/2009 |
| WO | WO 2010/003877 | 1/2010 |
| WO | WO 2010/003923 | 1/2010 |
| WO | WO 2010/005048 | 1/2010 |
| WO | WO 2010/072781 | 7/2010 |
| WO | WO 2011/161130 | 12/2011 |
| WO | WO 2012/059441 | 5/2012 |
| WO | WO 2012/151512 | 11/2012 |

OTHER PUBLICATIONS

International Search Report prepared in International Application No. PCT/EP2010/055773, filed Apr. 29, 2010.

International Preliminary Report on Patentability from corresponding International Application No. PCT/EP2010/055773, filed Apr. 29, 2010.

Hatanaka, Y. et al., "An Improved Synthesis of 4-[3-(Trifluoromethyl)-3H-Diazirin-3-YL]Benzoic Acid for Photoaffinity Labeling", Heterocycles, (1993), pp. 997-1004, vol. 35, No. 2.

Nader, B. et al., "A Novel Fluoride Ion Mediated Olefination of Electron-Deficient Aryl Ketones by Alkanesulfonyl Halides", J. Org. Chem. (1994), pp. 2898-2901, vol. 59.

Doamaral et al., "AntiMalarial Activity of Guanyl Hydrazone Salts of Aromatic Ketones Part 2 Development of Active Poly Halo Derivatives," Journal of Medicinal Chemistry, vol. 14, No. 9, (1971), pp. 862-866.

Beech, "Preparation of Aromatic Aldehydes and Ketones from Diazonium Salts," Journal of the Chemical Society, (1954), pp. 1297-1302.

Jolad et al., "2-bromo-4-methylbenzaldehyde (*p*-tolualdehyde, 2-bromo-)," Organic Synthesis—Collective Volumes, eds. John Wiley and Sons, vol. 46, (1966), pp. 13-16.

Schoenberg, A., et al., "Palladium-Catalyzed Amidation of Aryl, Hereocyclic and Vinylic Halides", J. Org. Chem. 1974, p. 3327-3331, vol. 39, No. 23.

Office action dated Feb. 27, 2014 from U.S. Appl. No. 13/805,559.

* cited by examiner

PROCESS FOR PREPARING SUBSTITUTED ISOXAZOLINE COMPOUNDS AND THEIR PRECURSORS

This application is a National Stage application of International Application No. PCT/EP2010/055773 filed Apr. 29, 2010, the entire contents of which is hereby incorporated herein by reference. This application also claims priority under 35 U.S.C. §119 to European Patent Application No. 09159246.9, filed Apr. 30, 2009, the entire contents of which is hereby incorporated herein by reference.

The present invention relates to a new process for preparing halogenated styrene compounds, which are precursor in the synthesis of substituted isoxazoline compounds.

Because of their pesticidal activity, substituted isoxazoline compounds are interesting compounds for a broad use, e.g. in agriculture or for animal health purposes.

Therefore there is an ongoing need of the industry to provide methods of preparation of such substituted isoxazoline compounds, having improved characteristics in comparison to what is established in the art. Those characteristics includes process steps, which facilitate the safe, enviromental friendly and economically attractive preparation of substituted isoxazline compounds.

Accordingly, it is an object of the present invention to provide such new process for preparing substitiuted isoxazoline compounds, which avoids disadvantages of the art.

Surprisingly, it has now been found a new and inventive method for the synthesis of halogenated styrene compounds of formula (VIII)

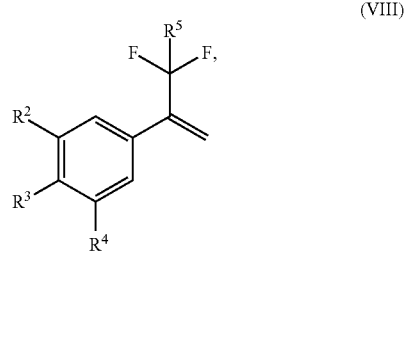

(VIII)

which are intermediate compounds for the synthesis of substituted isoxazoline compounds of formula (I), and thereby the latter can be accomplished on a large scale with the application of readily accessible starting materials and reagents, which makes the process less expensive, less time consuming, less complicated and therefore advantageous over those described in the art.

Furthermore, the facilitated process of preparation reduces multiple steps to fewer steps and requires therefore less energy, and is therefore also enviromental friendly. And, in addition, the process is more convergent and because of the lower number of steps compared to the published processes, is easier to acess and perform.

The substituted isoxazoline compounds prepared according to the new process of the present invention are of formula (I)

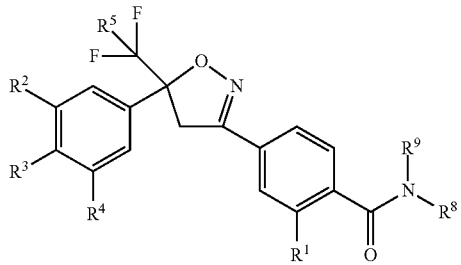

(I)

wherein $R^1$ is selected from H, $CH_3$, $CF_3$, $CH_2CH_3$, $CH_2CF_3$, Cl, Br, I, CN, $NO_2$, $SF_5$, $OCH_3$, $OCF_3$ or $OCHF_2$ $R^2$ is selected from H, F, Cl, Br, I or $CF_3$;

$R^3$ is selected from H, F, Cl, Br or CN;

$R^4$ is selected from H, F, Cl, Br, I or $CF_3$;

$R^5$ is selected from H, F, Cl or $CF_3$;

$R^8$ is selected from H, $C_1$-$C_6$-alkyl, optionally substituted with n substituents $R^{10}$, or Z-A, and wherein Z is a chemical bond, $CH_2$, $CH_2CH_2$ or C=O and A is selected from the group consisting of

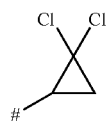

A-1

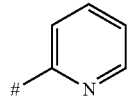

A-2

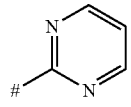

A-3

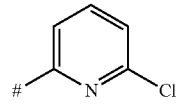

A-4

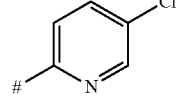

A-5

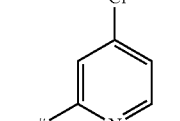

A-6

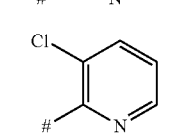

A-7

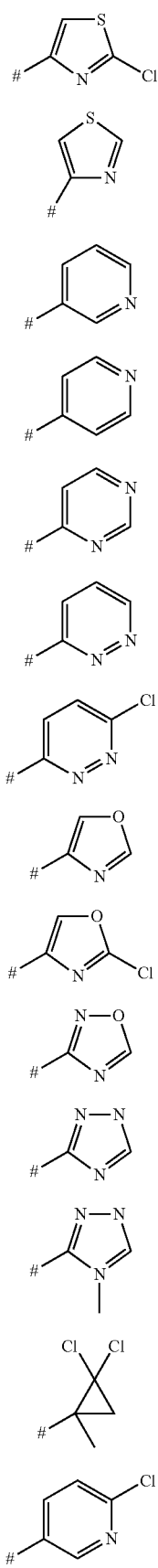
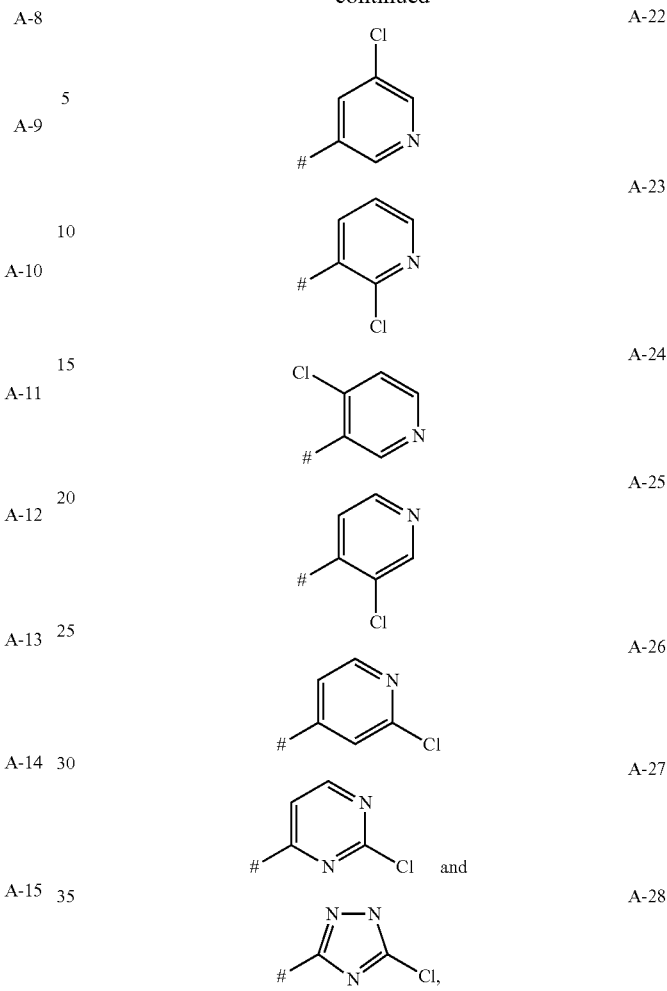

and wherein the "#" in the formulae of variables A indicate the bond to Z,
or
wherein
n is an integer selected from 1, 2, 3 or 4 and
each $R^{10}$ is independently from the value of n selected from the group consisting of hydrogen, halogen, cyano, azido, nitro, —SCN, $SF_5$, $C_1$-$C_6$-alkyl, $C_1$-$C_6$-haloalkyl, $C_1$-$C_6$-alkoxy-$C_1$-$C_6$-alkyl, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, —Si($R^{17}$)$_2$$R^{18}$, —$OR^{11}$,
—$OSO_2R^{11}$, —$SR^{11}$, —S(O)$_m$$R^{11}$, —S(O)$_n$N($R^{12}$)$R^{13}$, —N($R^{12}$)$R^{13}$, —C(=O)N($R^{12}$)$R^{13}$,
—C(=S)N($R^{12}$)$R^{13}$, —C(=O)$OR^{11}$, phenyl which may be substituted by 1, 2, 3, 4 or 5 radicals $R^{14}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{14}$;
or two vicinally bound radicals $R^{10}$ together form a group selected from =$CR^{15}R^{16}$, =S(O)$_m$$R^{11}$, =S(O)$_m$N($R^{12}$)$R^{13}$, =$NR^{12}$, =$NOR^{11}$ and =$NNR^{12}$;
or two radicals $R^{10}$, together with the carbon atoms to which they are bound, form a 3-, 4-, 5-, 6-, 7- or 8-membered saturated or partially unsaturated carbocyclic or heterocyclic ring containing 1, 2 or 3 heteroatoms or heteroatom groups selected from N, O, S, NO, SO and $SO_2$, as ring members;

and wherein $R^{11}$ is selected from the group consisting of hydrogen, cyano, $C_1$-$C_6$-alkyl, $C_2$-$C_6$-alkenyl, $C_2$-$C_6$-alkinyl, $C_3$-$C_8$-cycloalkyl, wherein the four last mentioned radicals may be unsubstituted, partially or fully halogenated and/or oxygenated; and/or may carry 1-2 radicals selected from $C_1$-$C_4$ alkoxy); $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tertbutyldimethylsilyl, phenyl, benzyl, pyridyl, phenoxy, it being possible for phenyl, benzyl, pyridyl and phenoxy to be unsubstituted, partially or fully halogenated and/or to carry 1-3 substituents selected from the group consisting of $C_1$-$C_6$-alkyl, $C_1$-$C_6$-haloalkyl, $C_1$-$C_6$-alkoxy, $C_1$-$C_6$ haloalkoxy); ($C_1$-$C_6$-alkoxy)carbonyl;

$R^{12}$, $R^{13}$ are, independently from one another, selected from the group consisting of hydrogen, cyano, $C_1$-$C_6$-alkyl, $C_2$-$C_6$-alkenyl, $C_2$-$C_6$-alkinyl, $C_3$-$C_8$-cycloalkyl, wherein the four last mentioned radicals may be unsubstituted, partially or fully halogenated and/or oxygenated; and/or may carry 1-2 radicals selected from C1-C4 alkoxy); $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tertbutyldimethylsilyl, phenyl, benzyl, pyridyl, phenoxy (it being possible for phenyl, benzyl, pyridyl and phenoxy to be unsubstituted, partially or fully halogenated and/or to carry 1-3 substituents selected from the group consisting of $C_1$-$C_6$-alkyl, $C_1$-$C_6$-haloalkyl, $C_1$-$C_6$-alkoxy, $C_1$-$C_6$ haloalkoxy); ($C_1$-$C_6$-alkoxy)carbonyl;

or, when $R^{12}$ and $R^{13}$ are adjacent on the same nitrogen, the two adjacent Rs may form a 3- to 7-membered saturated, partly saturated or unsaturated ring together with the nitrogen atom bearing them by forming a $C_2$-$C_6$ alkylene chain;

in this case, the alkylene chain may contain 1-2 oxygen atoms, sulfur atoms or nitrogen atoms, and may optionally be arbitrarily substituted with halogen atoms, $C_1$-$C_4$-haloalkyl, $C_1$-$C_4$-alkoxy, $C_1$-$C_4$-haloalkoxy;

each $R^{14}$ is, independently of each occurrence and independently from one another, selected from the group consisting of hydrogen, cyano, $C_1$-$C_6$-alkyl, $C_2$-$C_6$-alkenyl, $C_2$-$C_6$-alkinyl, $C_3$-$C_8$-cycloalkyl, wherein the four last mentioned radicals may be unsubstituted, partially or fully halogenated and/or oxygenated, and/or may carry 1-2 radicals selected from $C_1$-$C_4$-alkoxy, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tertbutyldimethylsilyl, phenyl, benzyl, pyridyl, phenoxy, it being possible for phenyl, benzyl, pyridyl and phenoxy to be unsubstituted, partially or fully halogenated and/or to carry 1-3 substituents selected from the group consisting of $C_1$-$C_6$-alkyl, $C_1$-$C_6$-haloalkyl, $C_1$-$C_6$-alkoxy, $C_1$-$C_6$ haloalkoxy); ($C_1$-$C_6$-alkoxy)carbonyl;

or two $R^{14}$ together may form =$C(C_1$-$C_4$-alky)$_2$, =$N(C_1$-$C_6$-alky), =$NO(C_1$-$C_6$-alky); =O;

or, when two $R^{14}$ are adjacent on a nitrogen atom, the two adjacent $R^{14}$s may form a 3- to 7-membered saturated, partly saturated or unsaturated ring together with the nitrogen atom bearing them by forming a $C_2$-$C_6$ alkylene chain; in this case, the alkylene chain may contain 1-2 oxygen atoms, sulfur atoms or nitrogen atoms, and may be arbitrarily substituted with halogen atoms, $C_1$-$C_4$-haloalkyl, $C_1$-$C_4$-alkoxy, $C_1$-$C_4$-haloalkoxy;

$R^{15}$, $R^{16}$ are, independent from one another, selected from the group consisting of hydrogen, halogen, cyano, azido, nitro, —SCN, $SF_5$, $C_1$-$C_6$-alkyl, $C_2$-$C_6$-alkenyl, $C_2$-$C_6$-alkinyl, $C_3$-$C_8$-cycloalkyl, wherein the four last mentioned radicals may be unsubstituted, partially or fully halogenated and/or oxgenated, and/or may carry 1-2 radicals selected from $C_1$-$C_4$ alkoxy; $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tertbutyldimethylsilyl, —OH, —SH, phenyl, benzyl, pyridyl, phenoxy, it being possible for phenyl, benzyl, pyridyl and phenoxy to be unsubstituted, partially or fully halogenated and/or to carry 1-3 substituents selected from the group consisting of $C_1$-$C_6$-alkyl, $C_1$-$C_6$-haloalkyl, $C_1$-$C_6$-alkoxy, $C_1$-$C_6$ haloalkoxy; ($C_1$-$C_6$-alkoxy)carbonyl, ($C_1$-$C_6$-alkyl)amino, di-($C_1$-$C_6$-alkyl)amino;

or $R^{15}$ and $R^{16}$ on the same carbon atom may together form =$C(C_1$-$C_4$-alky)$_2$, =$N(C_1$-$C_6$-alky), =$NO(C_1$-$C_6$-alky), =O;

$R^{17}$, $R^{18}$ are, independently of each other, selected from the group consisting of $C_1$-$C_4$-alkyl, $C_3$-$C_6$-cycloalkyl, $C_1$-$C_4$-alkoxy-$C_1$-$C_4$-alkyl, phenyl and benzyl;

$R^9$ is selected from H, $CH_3$, $CH_2CH_3$, $CH_2CH_2CH_3$, C(=O)$CH_3$ or C(=O)O$CH_3$;

Such substituted isoxazoline compounds have been described for their use as pesticides i.e. in WO 2005/085216 (corresponding to US 20070066617). Related insecticidal aryl isoxazolines have been further described in JP 2007-016017, WO 2007/026965, JP 2007-106756, WO 2007/070606, WO 2007/075459, WO 2007/079162, WO 2007/105814, WO 2007/125984, WO 2007/074789, JP 2008-156347, WO 2008/012027, WO 2008/019760, WO 2008/108448, JP 2008-239611, WO 2008/122375, WO 2008/130651, WO 2008/150393, WO2008/154528, WO 2009/002809, WO 2009/003075, WO 2009/24541, WO 2009/001942, WO 2009/063910 and WO 2010/005048.

Processes for the preparation of substituted isoxazoline compounds have been described in different publications, e.g. as in WO 2010/005048.

The synthesis of compounds of formula (I) has been, for example described in WO 2007/026965 and in JP 2008-133242, as shown in scheme 1 below, wherein an aryl bromide of formula (XI) was metalated with an organolithium reagent and then quenched with a boric acid ester to give boronic acids of formula (X). The latter was then coupled in a Suzuki reaction to give styrenes of formula (VIII). Alternatively, compounds of formula (VII) can also be provided by Grignard reaction of a compound (XI) as described in WO 2009/126668. The base mediated cycloaddition of styrenes of formula (VIII) with hydroxamic acid chlorides of formula (V) yields isoxazolines of formula (XV).

Compounds of formula (I) can then be prepared in a palladium catalyzed carbonylative amination reaction of isoxazolines of formula (XV) as described in scheme 1 below. This reaction has been described in WO 2007/079162 and WO2008/145740.

Scheme 1

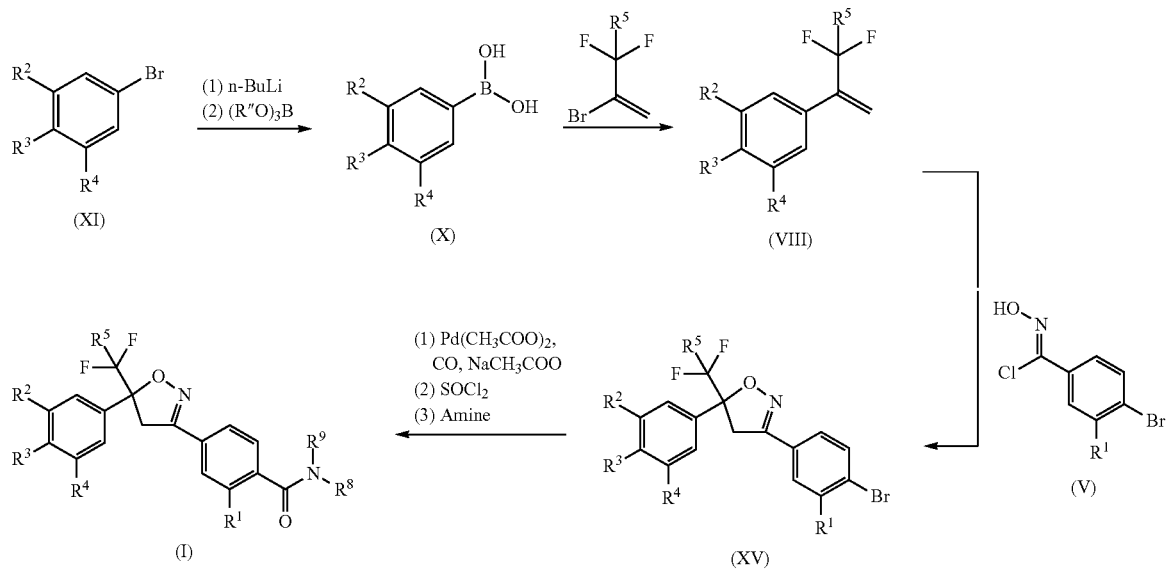

wherein R" is an alkyl group like methyl, ethyl, propyl, isopropyl, butyl or pheny.

Alternatively, compounds of formula (XV) can be synthesized from enones of formula (XVI) by reaction with hydroxylamine, as shown in scheme 2 below. Compounds of formula (XVI) can be synthesized from beta-hydroxy ketones of formula (XIV) by dehydration. Compounds of formula (XIV) can be prepared from acetophenones of formula (XIII) by an aldol reaction with compounds of formula (XVII), as for example described in JP 2008-133242. The corresponding acetophenones of formula (XVII) can be prepared as for example described in JP 2008-156347.

Scheme 2

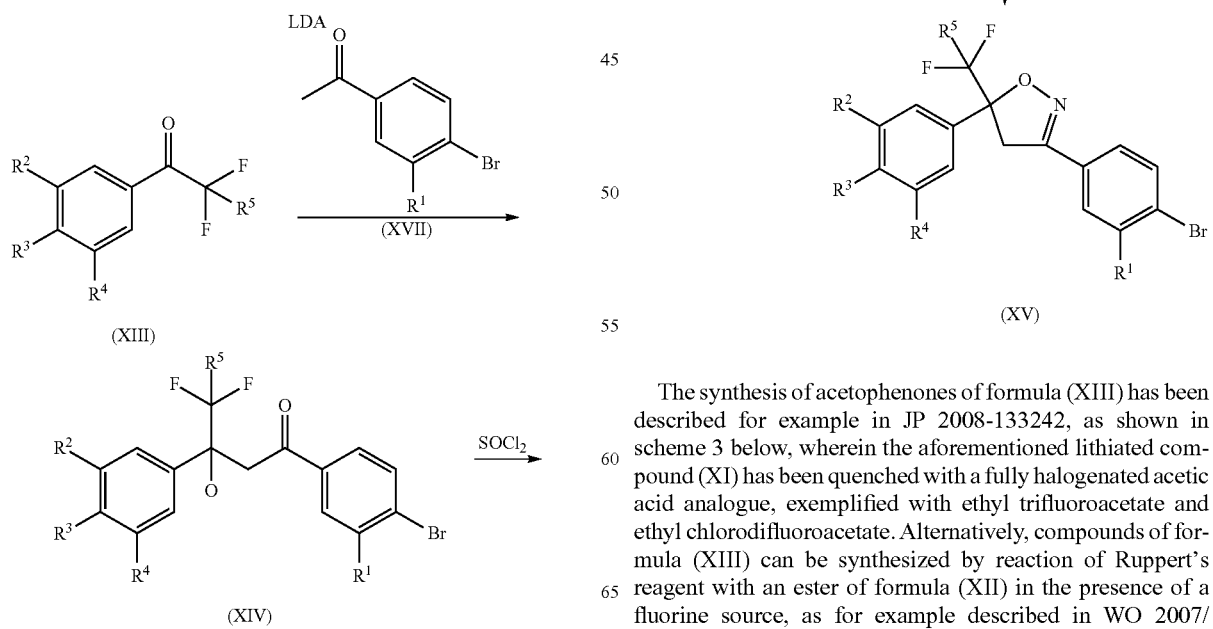

-continued

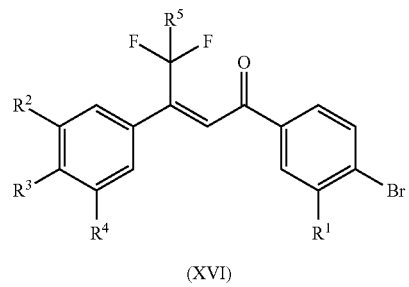

The synthesis of acetophenones of formula (XIII) has been described for example in JP 2008-133242, as shown in scheme 3 below, wherein the aforementioned lithiated compound (XI) has been quenched with a fully halogenated acetic acid analogue, exemplified with ethyl trifluoroacetate and ethyl chlorodifluoroacetate. Alternatively, compounds of formula (XIII) can be synthesized by reaction of Ruppert's reagent with an ester of formula (XII) in the presence of a fluorine source, as for example described in WO 2007/074789.

Scheme 3

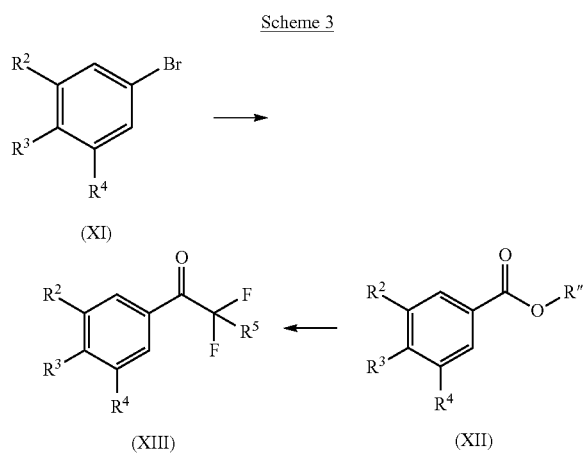

wherein R″ is an alkyl group like methyl, ethyl, propyl, isopropyl, butyl or phenyl.

The meaning of $R^1$, $R^2$, $R^3$, $R^4$, $R^5$, $R^8$ and $R^9$ for formulas used in schemes 1 to 3 is defined as for formula (I).

However, processes for the preparation of substituted isoxazoline compounds as previously described have several disadvantages.

The application of organolithium compounds, such as butyl lithium, represents a dangerous process step in terms of reaction safety. Especially, when used on a on a large scale production level.

Likewise, the availability of Ruppert's reagent on a large scale is limited. Therefore the process of preparation as described above is economically not attractive.

Furthermore, a facilitated process of preparation, which reduces multiple steps to fewer steps would require less energy, and would therefore be enviromental friendly.

Accordingly, it is an object of the present invention to provide such process for preparing substituted isoxazoline compounds, which avoids those disadvantages of the art.

Additionally, this new process allows for safer handling of the reaction since the use of organolithium compounds can be avoided.

PROCESS OF THE INVENTION

The present invention below relates to the process for preparing halogenated styrene compounds (VIII), which are important intermediate compounds in the synthesis of substituted isoaxzoline compounds of formula (I) as shown in scheme 4 below. The synthesis of compounds of formula (I) starts from acetophenones of formula (VII), which have been prepared by Grignard reaction of halogenides of formula (VI) with magnesium or a Grignard reagent and subsequent quenching with a halogenated acid derivative in an upstream process step. The desired styrenes of formula (VIII) according to the present invention are then prepared from the appropriate substituted acetophenone of formula (VII) via a Wittig reaction. Asides bromo anilines of formula (II) react upon a Sandmeyer reaction with formoxime—and, depending on the reaction conditions, either an aldehyde of formula (III), or an oxime of formula (IV) can be obtained. In case where aldehydes of formula (III) are obtained, a one step process leads to oximes of formula (IV). The latter oximes undergo a cycloaddition with styrenes of formula (VIII) either in a two-step process via hydroxamic acid chloride (V) as will be shown later on or a one pot reaction to directly give isoxazolines of formula (XV). Compounds of formula (I) can be then prepared in a palladium catalyzed carbonylative amination reaction of isoxazolines of formula (XV).

The bromo anilines of formula (II) mentioned above could also react upon a Sandmeyer reaction with acetaldoxime instead of formoxine and would result in a compound of formula (XVII) as described in scheme 2 above, wherein $R^6$ is $CH_3$, which is another useful intermediate compound for the preparation of compounds of formula (I). As mentioned above, this compound of formula (XVII) could then react with an acetophenone of formula (XIII) in an aldol reaction, and be further processed to compounds of formula (I).

Individual parts and steps of the process have been described in the art taken alone. The two-step process of the cycloaddition has been described i.e. in WO 2005/085216, JP 2007-016017, WO 2007/026965, WO 2007/079162, JP 2007-106756, WO 2007/105814, WO 2007/125984, WO 2008/012027, WO 2008/019760, WO 2008/108448, JP 2008-239611, WO 2008/122375, WO 2008/130651, WO 2009/002809, the one-pot process of the cycloaddition has been described i.e. in WO 2007/070606, WO 2007/075459, WO 2008/150393. The Grignard reaction has i.e. been described in Heterocycles 1993, 35, 2, 997-1004 or in WO 2009/126668. The cycloaddition has been described in WO 2007/070606 and WO 2007/075459. The final reaction step resulting in compounds of formula (I) has been described in WO 2007/079162 and WO2008/145740. The olefination reaction is known for example by Nader et al, J. Org. Chem. 1994, 59, 2898, but has never been described for halogenated derivatives such as halogenated acteophenons.

It was surprisingly found that the Wittig reaction on acetophenons is applicable for obtaining halogenated styrene compounds of formula (VIII), and for using the method in the synthesis of substituted isoaxzoline compounds.

Thus, the method of providing halogenated styrene compounds (VIII) and its incorporation in the combination and sequence of other individual steps of this advantageous process of preparation of substituted isoxazoline compounds has not been disclosed before. Therefore the process of the present invention is new and inventive over prior art.

Scheme 4

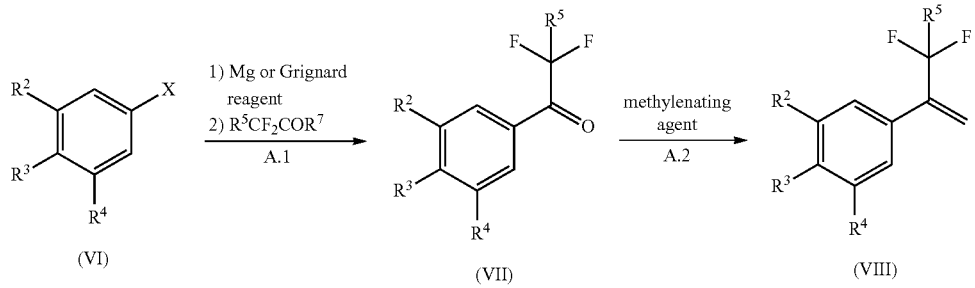

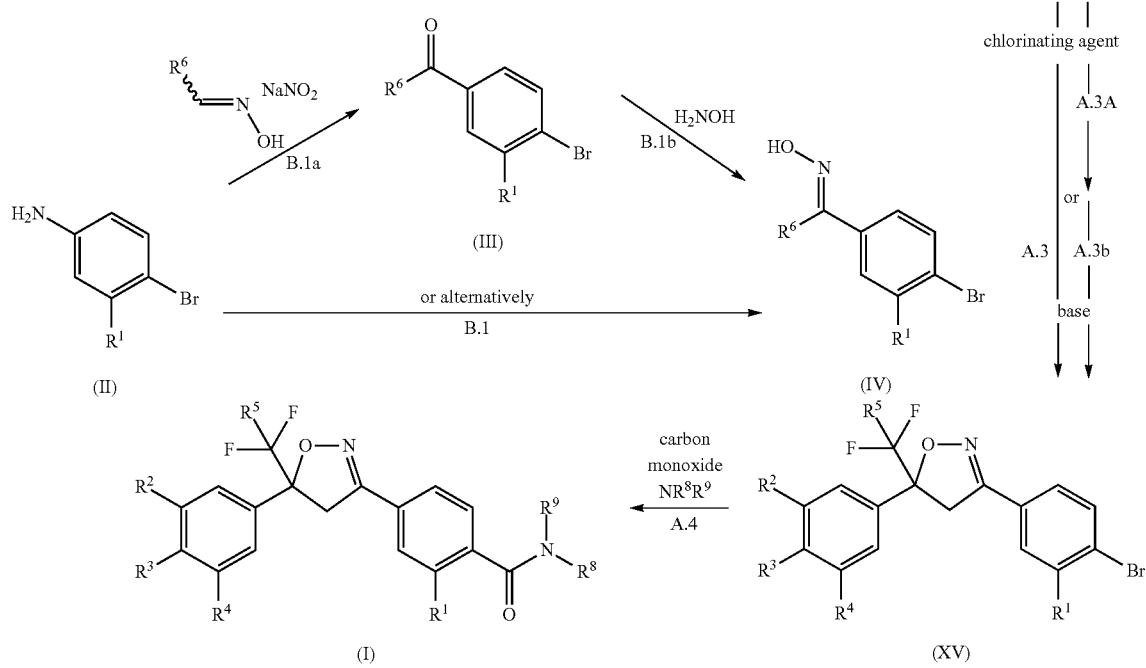

wherein in scheme 4:

$R^1$ to $R^5$ are defined as above, $R^6$ is H, and wherein the second step agent of A.1 is a di- and trifluoroacetic acid derivatives, $R^7$ is for example, but not limited to, OH, $F_3CCOO$, halogen, $C_1$-$C_6$-alkoxy, $N(CH_3)_2$, $N(C_2H_5)_2$, $N(OCH_3)CH_3$, piperidine, morpholine or piperazine, and wherein the last three radicals are bound via their nitrogen atom;

The terms for organic groups used in the definition of the variables, such as, for example, the term "halogen", are collective terms which represent the individual members of these groups of organic moieties. In each case, the prefix $C_x$-$C_y$ denotes the number of possible carbon atoms.

The term "halogen" refers in each case to fluorine, chlorine, bromine or iodine, especially fluorine or chlorine.

Examples of other meanings are:

The term "alkyl", as used in $C_1$-$C_8$-alkyl and in the terms $C_1$-$C_4$-alkoxy, $C_1$-$C_4$-alkoxy-$C_1$-$C_2$-alkyl and $C_1$-$C_4$-alkylthio, refers to a saturated straight-chain or branched hydrocarbon group comprising especially 1 to 8 carbon atoms or 1 to 4 carbon atoms, for example methyl, ethyl, propyl, 1-methylethyl, butyl, 1-methylpropyl, 2-methylpropyl, 1,1-dimethylethyl, pentyl, 1-methylbutyl, 2-ethylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, 1-methylhexyl, 2-methylhexyl, 3-methylhexyl, 4-methylhexyl, 5-methylhexyl, 1,1-dimethylpentyl, 1,2-dimethylpentyl, 1,3-dimethylpentyl, 1,4-dimethylpentyl, 2,2-dimethylpentyl, 2,3-dimethylpentyl, 2,4-dimethylpentyl, 3,3-dimethylpentyl, 3,4-dimethylpentyl, 1-ethylpentyl, 2-ethylpentyl, 1,1,2-trimethylbutyl, 1,1,3-trimethylbutyl, 1,2,2-trimethylbutyl, 1,2,3-trimethylbutyl, 1,3,3-trimethylbutyl, 2,2,3-trimethylbutyl, 2,3,3-trimethylbutyl, 1-ethyl-1-methylbutyl, 1-ethyl-2-methylbutyl, 1-ethyl-3-methylbutyl, octyl, 1-methylheptyl, 2-methylheptyl, 3-methylheptyl, 4-methylheptyl, 5-methylheptyl, 6-methylheptyl and their isomers. $C_1$-$C_4$-alkyl comprises, for example, methyl, ethyl, propyl, 1-methylethyl, butyl, 1-methylpropyl, 2-methylpropyl or 1,1-dimethylethyl.

The term "$C_2$-$C_6$-alkenyl" refers to monounsaturated straight-chain or branched hydrocarbon radicals having 2 to 6 carbon atoms, preferably 2 to 4 carbon atoms, and a C—C double bond in any position, for example $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl.

The term "$C_2$-$C_6$-alkynyl" refers to monounsaturated straight-chain or branched hydrocarbon radicals having 2 to 6 carbon atoms, preferably 2 to 4 carbon atoms, and a C—C triple bond in any position, for example $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, dimethyl-3-butynyl, 3,3-dimethyl-1-butynyl, 3,3-dimethyl-2-butynyl, ethyl-2-butynyl, 1-ethyl-3-butynyl, 2-ethyl-3-butynyl or 1-ethyl-1-methyl-2-propynyl.

The term "$C_1$-$C_6$-alkoxy" refers to straight-chain or branched saturated alkyl groups comprising 1 to 6 carbon atoms, which groups are attached via an oxygen atom. Examples include $C_1$-$C_6$-alkoxy, such as, for example, methoxy, ethoxy, $OCH_2$—$C_2H_5$, $OCH(CH_3)_2$, n-butoxy, $OCH(CH_3)$—$C_2H_5$, $OCH_2$—$CH(CH_3)_2$ and $OC(CH_3)_3$.

The term "$C_1$-$C_6$-alkylthio" refers to straight-chain or branched saturated alkyl groups comprising 1 to 6 carbon atoms, which groups are attached via a sulfur atom. Examples include $C_1$-$C_6$-alkylthio, such as, for example, methylthio, ethylthio, $SCH_2$—$C_2H_5$, $SCH(CH_3)_2$, n-butylthio, $SCH(CH_3)$—$C_2H_5$, $SCH_2$—$CH(CH_3)_2$ and $SC(CH_3)_3$.

The term "$C_1$-$C_6$-haloalkyl", as used herein and in the haloalkyl moieties of $C_1$-$C_6$-haloalkoxy and $C_1$-$C_6$-haloalkylthio, refers to straight-chain or branched alkyl groups having 1 to 6 carbon atoms, where some or all of the hydrogen atoms of these groups are replaced by halogen atoms, for example $C_1$-$C_6$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, heptafluoroisopropyl, etc.

The term "$C_2$-$C_6$-haloalkenyl" as used herein, which is also expressed as "$C_1$-$C_6$-alkenyl which is partially or fully halogenated", and the haloalkenyl moieties in haloalkenyloxy, haloalkenylcarbonyl and the like refers to unsaturated straight-chain or branched hydrocarbon radicals having 2 to 4 ("$C_2$-$C_4$-haloalkenyl") or 2 to 6 ("$C_2$-$C_6$-haloalkenyl") carbon atoms and a double bond in any position (as mentioned above), where some or all of the hydrogen atoms in these groups are replaced by halogen atoms as mentioned above, in particular fluorine, chlorine and bromine, for example chlorovinyl, chloroallyl and the like.

The term "$C_2$-$C_6$-haloalkynyl" as used herein, which is also expressed as "$C_1$-$C_6$-alkynyl which is partially or fully halogenated", and the haloalkynyl moieties in haloalkynyloxy, haloalkynylcarbonyl and the like refers to unsaturated straight-chain or branched hydrocarbon radicals having 2 to 4 ("$C_2$-$C_4$-haloalkynyl"), 3 to 4 ("$C_3$-$C_4$-haloalkynyl"), 2 to 6 ("$C_2$-$C_6$-haloalkynyl") or 3 to 6 ("$C_3$-$C_6$-haloalkynyl"), carbon atoms and one or two triple bonds in any position (as mentioned above), where some or all of the hydrogen atoms in these groups are replaced by halogen atoms as mentioned above, in particular fluorine, chlorine and bromine.

The term "$C_1$-$C_6$-haloalkoxy" refers to $C_1$-$C_6$-haloalkyl groups, as defined above, which are attached via an oxygen atom. Examples include mono-, di- and trifluoromethoxy, mono-, di- and trichloromethoxy, 1-fluoroethoxy, 1-chloroethoxy, 2-fluoroethoxy, 2-chloroethoxy, 1,1-difluoroethoxy, 1,1-dichloroethoxy, 1,2-difluoroethoxy, 1,2-dichloroethoxy, 2,2-difluoroethoxy, 2,2-dichloroethoxy, 2,2,2-trifluoroethoxy, 1,1,2,2-tetrafluoroethoxy, 2,2,2-trichloroethoxy, 1,1,1,2,3,3-hexafluoroisopropoxy, 1,1,2,3,3,3-hexafluoroisopropoxy, 2-chloro-1,1,2-trifluoroethoxy or heptafluoroisopropoxy.

The term "$C_1$-$C_6$-haloalkylthio" refers to $C_1$-$C_6$-haloalkyl groups, as defined above, which are attached via a sulfur atom. Examples include mono-, di- and trifluoromethylthio, mono-di- and trichloromethylthio, 1-fluoroethylthio, 1-chloroethylthio, 2-fluoroethylthio, 2-chloroethylthio, 1,1-difluoroethylthio, 1,1-dichloroethylthio, 1,2-difluoroethylthio, 1,2-dichloroethylthio, 2,2-difluoroethylthio, 2,2-dichloroethylthio, 2,2,2-trifluoroethylthio, 1,1,2,2-tetrafluoroethylthio, 2,2,2-trichloroethylthio, 1,1,1,2,3,3-hexafluoroisopropylthio, 1,1,2,3,3,3-hexafluoroisopropylthio, 2-chloro-1,1,2-trifluoroethylthio or heptafluoroisopropylthio.

The term "$C_1$-$C_2$-alkylsulfinyl" is a $C_1$-$C_2$-alkyl group, as defined above, attached via a sulfinyl [S(O)] group. The term "$C_1$-$C_4$-alkylsulfinyl" is a $C_1$-$C_4$-alkyl group, as defined above, attached via a sulfinyl [S(O)] group. The term "$C_1$-$C_6$-alkylsulfinyl" is a $C_1$-$C_6$-alkyl group, as defined above, attached via a sulfinyl [S(O)] group. The term "$C_1$-$C_{10}$-alkylsulfinyl" is a $C_1$-$C_{10}$-alkyl group, as defined above, attached via a sulfinyl [S(O)] group. $C_1$-$C_2$-Alkylsulfinyl is methylsulfinyl or ethylsulfinyl. $C_1$-$C_4$-Alkylsulfinyl is additionally, for example, n-propylsulfinyl, 1-methylethylsulfinyl (isopropylsulfinyl), butylsulfinyl, 1-methylpropylsulfinyl (sec-butylsulfinyl), 2-methylpropylsulfinyl (isobutylsulfinyl) or 1,1-dimethylethylsulfinyl (tert-butylsulfinyl). $C_1$-$C_6$-Alkylsulfinyl is additionally, for example, pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl. $C_1$-$C_8$-Alkylsulfinyl is additionally, for example, heptylsulfinyl, octylsulfinyl, 2-ethylhexylsulfinyl and positional isomers thereof. $C_1$-$C_{10}$-Alkylsulfinyl is additionally, for example, nonylsulfinyl, decylsulfinyl and positional isomers thereof.

The term "$C_1$-$C_2$-haloalkylsulfinyl" is a $C_1$-$C_2$-haloalkyl group, as defined above, attached via a sulfinyl [S(O)] group. The term "$C_1$-$C_4$-haloalkylsulfinyl" is a $C_1$-$C_4$-haloalkyl group, as defined above, attached via a sulfinyl [S(O)] group. The term "$C_1$-$C_6$-haloalkylsulfinyl" is a $C_1$-$C_6$-haloalkyl group, as defined above, attached via a sulfinyl [S(O)] group. The term "$C_1$-$C_{10}$-haloalkylsulfinyl" is a $C_1$-$C_{10}$-haloalkyl group, as defined above, attached via a sulfinyl [S(O)] group. $C_1$-$C_2$-Haloalkylsulfinyl is, for example, $OCH_2F$, $OCHF_2$, $OCF_3$, $OCH_2Cl$, $OCHCl_2$, $OCCl_3$, chlorofluoromethylsulfinyl, dichlorofluoromethylsulfinyl, chlorodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2-chloro-2-fluoroethylsulfinyl, 2-chloro-2,2-difluoroethylsulfinyl, 2,2-dichloro-2-fluoroethylsulfinyl, 2,2,2-trichloroethylsulfinyl or $OC_2F_5$. $C_1$-$C_4$-Haloalkylsulfinyl is additionally, for example, 2-fluoropropylsulfinyl, 3-fluoropropylsulfinyl, 2,2- difluoropropylsulfinyl, 2,3-difluoropropylsulfinyl, 2-chloropropylsulfinyl, 3-chloropropylsulfinyl, 2,3-dichloropropylsulfinyl, 2-bromopropylsulfinyl, 3-bromopropylsulfinyl, 3,3,3-trifluoropropylsulfinyl, 3,3,3-trichloropropylsulfinyl, $OCH_2$—$C_2F_5$, $OCF_2$—$C_2F_5$, 1-($CH_2F$)-2-fluoroethylsulfinyl, 1-($CH_2Cl$)-2-chloroethylsulfinyl, 1-($CH_2Br$)-2-bromoethylsulfinyl, 4-fluorobutylsulfinyl, 4-chlorobutylsulfinyl, 4-bromobutylsulfinyl or nonafluorobutylsulfinyl. $C_1$-$C_6$-Haloalkylsulfinyl is additionally, for example, 5-fluoropentylsulfinyl, 5-chloropentylsulfinyl, 5-brompentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl or dodecafluorohexylsulfinyl.

The term "$C_1$-$C_2$-alkylsulfonyl" is a $C_1$-$C_2$-alkyl group, as defined above, attached via a sulfonyl [$S(O)_2$] group. The term "$C_1$-$C_4$-alkylsulfonyl" is a $C_1$-$C_4$-alkyl group, as defined above, attached via a sulfonyl [$S(O)_2$] group. The term "$C_1$-$C_6$-alkylsulfonyl" is a $C_1$-$C_6$-alkyl group, as defined above, attached via a sulfonyl [$S(O)_2$] group. The term "$C_1$-$C_{10}$-alkylsulfonyl" is a $C_1$-$C_{10}$-alkyl group, as defined above, attached via a sulfonyl [$S(O)_2$] group. $C_1$-$C_2$-Alkylsulfonyl is methylsulfonyl or ethylsulfonyl. $C_1$-$C_4$-Alkylsulfonyl is additionally, for example, n-propylsulfonyl, 1-methylethylsulfonyl (isopropylsulfonyl), butylsulfonyl, 1-methylpropylsulfonyl (sec-butylsulfonyl), 2-methylpropylsulfonyl (isobutylsulfonyl) or 1,1-dimethylethylsulfonyl (tert-butylsulfonyl). $C_1$-$C_6$-Alkylsulfonyl is additionally, for example, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl. $C_1$-$C_8$-Alkylsulfonyl is additionally, for example, heptylsulfonyl, octylsulfonyl, 2-ethylhexylsulfonyl and positional isomers thereof. $C_1$-$C_{10}$-Alkylsulfonyl is additionally, for example, nonylsulfonyl, decylsulfonyl and positional isomers thereof.

The term "$C_1$-$C_2$-haloalkylsulfonyl" is a $C_1$-$C_2$-haloalkyl group, as defined above, attached via a sulfonyl [$S(O)_2$] group. The term "$C_1$-$C_4$-haloalkylsulfonyl" is a $C_1$-$C_4$-haloalkyl group, as defined above, attached via a sulfonyl [$S(O)_2$] group. The term "$C_1$-$C_6$-haloalkylsulfonyl" is a $C_1$-$C_6$-haloalkyl group, as defined above, attached via a sulfonyl [$S(O)_2$] group. The term "$C_1$-$C_{10}$-haloalkylsulfonyl" is a $C_1$-$C_{10}$-haloalkyl group, as defined above, attached via a sulfonyl [$S(O)_2$] group. $C_1$-$C_2$-Haloalkylsulfonyl is, for example, $OCH_2F$, $OCHF_2$, $OCF_3$, $OCH_2Cl$, $OCHCl_2$, $OCCl_3$, chlorofluoromethylsulfonyl, dichlorofluoromethylsulfonyl, chlorodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl or $OC_2F_5$. $C_1$-$C_4$-Haloalkylsulfonyl is additionally, for example, 2-fluoropropylsulfonyl, 3-fluoropropylsulfonyl, 2,2-difluoropropylsulfonyl, 2,3-difluoropropylsulfonyl, 2-chloropropylsulfonyl, 3-chloropropylsulfonyl, 2,3-dichloropropylsulfonyl, 2-bromopropylsulfonyl, 3-bromopropylsulfonyl, 3,3,3-trifluoropropylsulfonyl, 3,3,3-trichloropropylsulfonyl, $OCH_2$—$C_2F_5$, $OCF_2$—$C_2F_5$, 1-($CH_2F$)-2-fluoroethylsulfonyl, 1-($CH_2Cl$)-2-chloroethylsulfonyl, 1-($CH_2Br$)-2-bromoethylsulfonyl, 4-fluorobutylsulfonyl, 4-chlorobutylsulfonyl, 4-bromobutylsulfonyl or nonafluorobutylsulfonyl. $C_1$-$C_6$-Haloalkylsulfonyl is additionally, for example, 5-fluoropentylsulfonyl, 5-chloropentylsulfonyl, 5-brompentylsulfonyl, 5-iodopentylsulfonyl, undecafluoropentylsulfonyl, 6-fluorohexylsulfonyl, 6-chlorohexylsulfonyl, 6-bromohexylsulfonyl, 6-iodohexylsulfonyl or dodecafluorohexylsulfonyl.

The term "$C_3$-$C_7$-cycloalkyl", as used herein, describes cyclic hydrocarbon radicals comprising 3 to 7 carbon atoms. Examples of cyclic radicals are cyclopropyl, cyclobutyl, cyclopentyl, cyclohexyl or cycloheptyl.

The term "$C_3$-$C_8$-halocycloalkyl" as used herein, which is also expressed as "$C_3$-$C_8$-cycloalkyl which is partially or fully halogenated", and the halocycloalkyl moieties in halocycloalkoxy, halocycloalkylcarbonyl and the like refers to mono- or bi- or polycyclic saturated hydrocarbon groups having 3 to 8 ("$C_3$-$C_8$-halocycloalkyl") or preferably 3 to 6 ("$C_3$-$C_6$-halocycloalkyl") carbon ring members (as mentioned above) in which some or all of the hydrogen atoms are replaced by halogen atoms as mentioned above, in particular fluorine, chlorine and bromine.

DETAILED DESCRIPTION OF THE INVENTION

The method for preparing halogenated styrene compounds of formula (VIII) and the further individual steps of the whole processes for providing substituted isoxazoline compounds of the formula (I) are shown below in further details.

The definitions of the substituents and variables correspond accordingly to the ones given for scheme 4 and compounds of formula (I) given above.

A.2 the Wittig Reaction of a Compound of the Formula (VII) to a Compound of Formula (VIII)

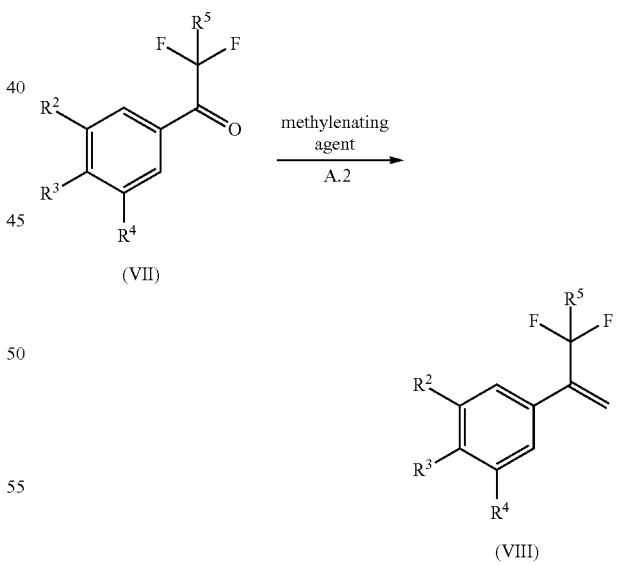

The term methylenating agent in this reaction refers to a reagent independently selected from dimethyltitanocene, diphenylmethylphosphine oxide, dimethoxymethylphosphine sulfide, pentamethylphosphonic diamide, dimethyl sulfoxide, (trialkylstannyl)(trimethylsilyl)methane, trimethylsilyl(phenylthio)methane, titanium tetrachloride and diiodomethane or dibromomethane, dichlorotitanocene and aluminum trimethyl, methylenetriphenylphosphine, trimethylsulfonium iodide, dichloro(cyclopentadienyl)zirconium and diiodomethane or dibromomethane dimethyl methanephosphonate, methanesulfonyl chloride, (chloromethyl)trimethylsilylane, diazomethyltrimethyl silane, Nysted's reagent or a precursor of a methylenating agent.

Olefination reactions of electron deficient aryl ketones, such as compounds of the general formula (VII) have been described in the art e.g. by Nader et al, J. Org. Chem. 1994, 59, 2898-2901.

However, the application of the described method towards substrates of the core of the present invention can not be transferred in good yields. For example a sample reaction employing 3,5-dichloro-2,2,2-trifluoro acetophenone yielded only 26% of the desired product in 71% purity according to gas chromatographic analysis. Furthermore, the described method employs highly corrosive and toxic reagents, such as methane sulfonic acid chloride and potassium fluoride at high temperatures. In the course of such a reaction process, or upon accidental contact of the reaction mixture with traces of water, extremely harmful gases such as hydrogen fluoride or hydrogen chloride could develop. Such a process would require cost and labour intensive precaution installments as well as specific resistant and expensive vessel materials.

It has now surprisingly been found, that a Wittig reaction process for preparing halogenated styrene compounds offers several advantages over the art. The disadvantages of the olefination reaction as described above are avoided, and furthermore the yield of the desired product is better than compared to the olefination reaction.

Preferably the methylenating agent is obtained by a precursor of the methylenating agent, which is freshly powdered triphenylmethyl phosphinium iodide, triphenylmethyl phosphinium bromide or triphenylmethyl phosphinium chloride. Especially preferred are triphenylmethyl phosphinium bromide or triphenylmethyl phosphinium chloride. The prescursor is is activated by the addition of a base The base for activating the prescursor of the methylenating agent can be taken from alkali metal alcoholates, such as but not limiting to potassium methoxide, sodium methoxide or potassium tert.-butoxide, organolithium reagents, lithium or sodium amides. Preferably alkali metal alcoholates are used.

An advantage of using potassium methoxide in comparison to potassium tert.-butoxide is e.g. that it is cheaper and the resulting methanol is much easier to be distilled off. Same applies to the use of sodium methoxide.

The methylenating agent is preferably employed in a molar ratio of from 1 to 1.5 per mol of the compound (VII). In particular, from 1.02-1.2 mol of a methylenating agent are employed per mol of the compound (VII).

The base for activating the prescursor is preferably also employed in a molar ratio of from 1 to 1.5 per mol of the compound (VII). In particular from 1.02-1.2 mol of a base are employed per mol of the compound (VII).

A further embodiment of the present invention is the order of addition of the reagents to the reaction. This was also found to have an impact on the isolated yield.

In a preferred embodiment the precursor is a phosphonium salt, and the precursor, the acetophenone of formula (VII) and the solvent are placed together in a reaction vessel and a solution of the base is added subsequently to this mixture.

Alternatively the base can also be added in solid form.

The reaction of a compound of the formula (VII) with a methylenating agent to a compound of formula (VIII) is generally carried out at temperatures of from −78 to 110° C. In general, the upper temperature limits the boiling point of the solvent in question when the reaction is carried out under atmospheric pressure. Preferably the temperature is in the range of −20° C. to 100° C., more prefered the temperature range is between 0° C. and 80° C. and especially preferred between 20° C. and 70° C.

In the reaction of compounds of the formula (VII) with a methylenating agent the pressure is preferably in a range of from 0.9 to 2 bar, particularly preferably in a range of from 0.9 to 1.5 bar and especially in a range of from 0.9 to 1.1 bar.

The reaction of the compound of formula (VII) with a methylenating agent can be carried out in suitable solvents. Organic solvents suitable for the reaction are aromatic hydrocarbons, such as benzene, toluene, xylenes, cumene, chlorobenzene, dichlorobenzenes nitrobenzene, pyridine or tert-butylbenzene, aprotic polar solvents, for example cyclic or acyclic ethers, such as diethyl ether, tert-butyl methyl ether (MTBE), cyclopentyl methyl ether, tetrahydrofuran (THF), methyl THF or dioxane or aliphatic nitriles, such as acetonitrile or propionitrile, non-polar organic solvents like pentane, hexane, cyclohexane, heptane, octane, nonane and decane and also mixtures of the solvents mentioned above. The omission of water as a solvent facilitates recycling purposes and avoid the production of waste water.

The reaction is preferably carried out in aromatic hydrocarbons, such as benzene, toluene, xylenes, cumene, chlorobenzene, dichlorobenzenes, nitrobenzene, pyridine or tert-butylbenzene, aprotic polar solvents, for example cyclic or acyclic ethers, such as diethyl ether, tert-butyl methyl ether (MTBE), cyclopentyl methyl ether, tetrahydrofuran (THF), methyl THF or dioxane. Especially preferred are diethyl ether and THF.

In a further preferred embodiment after completion of the reaction, the solvent is distilled off and a non-polar solvent is added to dissolve the product and precipitate triphenylphosphine oxide. The latter can be filtered off for recycling purposes. Additionally, an organic salts resulting from the reaction of the phosphonium precursor and the base are also precipitated. Those water-soluble salt can be easily washed off the triphenylphosphine oxide precipitate.

Work-up of the reaction mixture and isolation of the compound of formula (VIII) are carried out in a customary manner, for example by removing the solvent, for example by distillation or by aqueous extractive work-up or by a combination of these measures. Further purification can be carried out, for example, by crystallization or by chromatography. However, frequently, the product is already obtained in a purity which does not require further purification steps.

Out of the reaction mixtures obtained from the reaction of compounds of the formula (VII) with a methylenating agent are optionally subjected to aqueous work-up, i.e. the reaction mixture obtained is brought into contact with water or an aqueous solution. After neutralization of the water-containing reaction mixtures obtained in this manner, the halogenated styrene compounds of the formula (VIII) can generally be isolated by extraction with an organic solvent such as mono and dichlorobenzene, toluene, xylene and mesitylene and subsequent removal of the organic solvent. If appropriate, especially when water-miscible solvents are used for the reaction, it may be advantageous to remove at least some of the solvent prior to the extraction, for example by distillation.

In a preferred embodiment, the work-up is done under non-aqueous conditions.

Alternatively the halogenated styrene compound (VIII) can be distilled from the non-polar solvent, in the case that the boiling point of the non-polar solvent is higher than the boiling point of the product. In the case of a lower boiling point of the non-polar solvent, the solvent has to be evaporated. The product can be distilled off from the distillation sump.

For the applying the reaction of A.2 it is also possible to use the crude products of the compounds of formula (VII) as obtained from the Grignard reaction described under A1 below without further work-up. Such reaction product compounds of formula (VII) may optionally contain small amounts of the hydrolysis side products from the Grignard reagents. However, the halogenated styrene compounds (VIII) have a higher boiling point than the respective hydrolysis products resulting from step (A 1). Therefore an easy separation from such side hydrolysis products is possible by distillation.

A. 1. the Upstream Grignard Reaction of a Compound of the Formula (VI) to a Compound of Formula (VII)

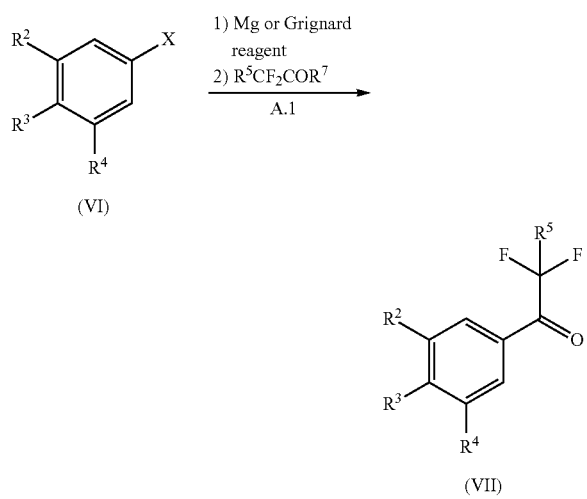

The reaction of a compound of the formula (VI), wherein X is halogen, to a compound of formula (VII) starts with the Grignard reaction.

The first step agent refers to a reagent independently selected from magnesium (turnings or powder) or a Grignard reagent. In case of magnesium, the magnesium can activated by reagents like iodine, bromine, dibromo ethane, monobromo ethane Grignard reagents suitable for the reaction are alkyl magnesium halogenides for example methyl magnesium chloride, methyl magnesium bromide, methyl magnesium iodide, ethyl magnesium chloride, ethyl magnesium bromide, ethyl magnesium iodide, propyl magnesium chloride, propyl magnesium bromide, propyl magnesium iodide, isopropyl magnesium chloride, isopropyl magnesium bromide, isopropyl magnesium iodide, butyl magnesium chloride, butyl magnesium bromide, butyl magnesium iodide, sec-butyl magnesium chloride, sec-butyl magnesium bromide, sec-butyl magnesium iodide, tert-butyl magnesium chloride, tert-butyl magnesium bromide, tert-butyl magnesium iodide, isobutyl magnesium chloride, isobutyl magnesium bromide and isobutyl magnesium iodide.

The reaction is preferably carried out with methyl magnesium chloride, methyl magnesium bromide, ethyl magnesium chloride, ethyl magnesium bromide, propyl magnesium chloride, propyl magnesium bromide, isopropyl magnesium chloride, isopropyl magnesium bromide, butyl magnesium chloride, butyl magnesium bromide, sec-butyl magnesium chloride, sec-butyl magnesium bromide, tert-butyl magnesium chloride, tert-butyl magnesium bromide, isobutyl magnesium chloride and isobutyl magnesium bromide.

The reaction is more preferably carried out with magnesium, methyl magnesium chloride, methyl magnesium bromide, isopropyl magnesium chloride, isopropyl magnesium bromide, tert-butyl magnesium chloride and tert-butyl magnesium bromide.

The halogen of the compound of formula (VI) is preferably Cl or Br.

The second step agent refers to a reagent independently selected from di- and trifluoroacetic acid derivatives. Suitable derivatives for the reaction are di- and trifluoroacetyl chlorides, bromides and fluorides as well as di- and trifluoroacetic acid alkylesters, wherein the di- and trifluoroacetic acid alkylesters can be di- and trifluoroacetic acid methyl esters and ethyl esters, further di- and trifluoroacetic acid anhydrides and di- and trifluoroacetamides, especially N,O-dimethylhydroxyl amides, dimethylamides, diethylamides, dibutylamides, morpholine amides and piperidine amides.

The second step reaction is preferably carried out with di- and trifluoroacetyl chlorides, bromides and fluorides as well as di- and trifluoroacetic acid alkylesters, di- and trifluoroacetic acid alkylesters can be di- and trifluoroacetic acid methyl esters and ethyl esters.

The Grignard reaction of a compound of the formula (VI) with magnesium or a Grignard reagent and an electrophile to a compound of formula (VII) is preferably carried out at temperatures of from −78 to 110° C. In general, the upper temperature limits the boiling point of the solvent in question when the reaction is carried out under atmospheric pressure. The first step (Grignard reaction) of the reaction is preferably carried out at temperatures of −30 to 110° C. The second step (electrophile addition) is preferably carried out at temperatures of −78° C. to 50° C.

In the reaction of compounds of the formula (VI) with magnesium or a Grignard reagent (first step) the pressure is preferably in a range of from 0.9 to 2 bar, particularly preferably in a range of from 0.9 to 1.5 bar and especially in a range of from 0.9 to 1.1 bar.

In the reaction of compounds of the first step with electrophiles (second step) the pressure is preferably in a range of from 0.9 to 200 bar, particularly preferably in a range of from 0.9 to 100 bar and especially in a range of from 0.9 to 50 bar.

The magnesium or an Grignard reagent is preferably employed in a molar ratio of from 0.9 to 2 mol per mol of the compound (VI). Preferably, from 0.9 to 1.2 mol, in particular from about 0.95 to 1.1 mol, of magnesium or a Grignard reagent are employed per mol of the compound (VI).

The electropiles are preferably employed in a molar ratio of from 0.9 to 5 mol per mol of the compound (VI). Preferably, from 0.9 to 2 mol, in particular from about 0.95 to 1.5 mol, of electrophiles are employed per mol of the compound (VI).

The reaction of the compound of formula (VI), with magnesium or a Grignard reagent and an electrophile can be carried out in organic solvents. Organic solvents suitable for the reaction are aprotic polar and unpolar solvents, for example aromatic hydrocarbons, such as benzene, toluene, xylenes, cumene, chlorobenzene, nitrobenzene, tert-butylbenzene, aprotic polar solvents, for example cyclic or acyclic ethers, such as diethyl ether, tert-butyl methyl ether (MTBE), cyclopentyl methyl ether tetrahydrofufan (THF) or dioxane or, and also mixtures of the solvents mentioned above.

The reaction is preferably carried out in aromatic hydrocarbons, such as benzene, toluene, xylenes, cumene, chlorobenzene, nitrobenzene, or tert-butylbenzene, aprotic polar solvents, for example cyclic or acyclic ethers, such as diethyl ether, tert-butyl methyl ether (MTBE), cyclopentyl methyl ether, tetrahydrofuran (THF) or dioxane.

Work-up of the reaction mixture and isolation of the compound of formula (VIII) are carried out in a customary manner, for example by removing the solvent, for example by distillation or by aqueous extractive work-up or by a combination of these measures. Further purification can be carried out, for example, by crystallization or by chromatography. However, frequently, the product is already obtained in a purity which does not require further purification steps.

The reaction mixtures obtained in the reaction of compounds of the formula (VI) with Grignard reagent and an electrophile are generally subjected to aqueous work-up, i.e. the reaction mixture obtained is brought into contact with a aqueous acid or an aqueous solution of $NH_4Cl$. After acidification of the water-containing reaction mixtures obtained in this manner, the compounds of the formula (VII) can generally be isolated by extraction with an organic solvent and subsequent removal of the organic solvent. If appropriate, especially when water-miscible solvents are used for the reaction, it may be advantageous to remove at least some of the solvent prior to the extraction, for example by distillation.

A.3 the Subsequent Reaction of a Compound of the Formula (VIII) to a Compound of Formula (XV)

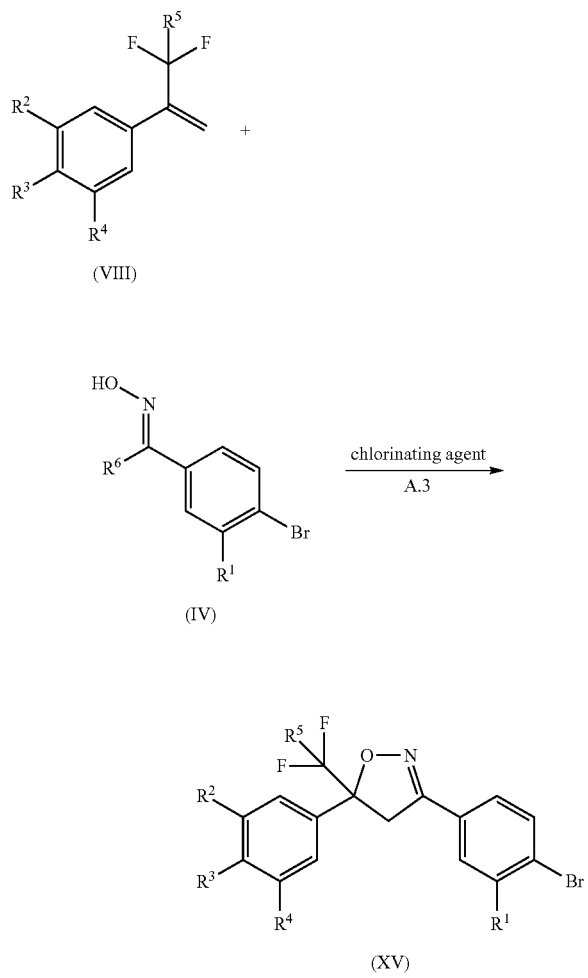

The term chlorinating agent refers to a reagent independently selected from chlorine, sodium hypochlorite, N-chlorosuccinimide or chloramine T.

The reaction of a compound of the formula (IV) with a chlorinating agent in the presence of a compound of formula (VIII) to a compound of formula (XV) is preferably carried out at temperatures of from −20 to 120° C. In general, the upper temperature limits the boiling point of the solvent in question when the reaction is carried out under atmospheric pressure.

In the reaction of compounds of the formula (IV) with a chlorinating agent the pressure is preferably in a range of from 0.9 to 2 bar, particularly preferably in a range of from 0.9 to 1.5 bar and especially in a range of from 0.9 to 1.3 bar.

The chlorinating agent is preferably employed in a molar ratio of from 0.9 to 10 mol per mol of the compound (IV). Preferably, from 0.9 to 5 mol, in particular from about 0.95 to 2 mol, of a chlorinating agent are employed per mol of the compound (IV). The compound of formula (VIII) is preferably employed in a molar ratio of from 0.9 to 2 mol per mol of the compound (IV). Preferably, from 0.9 to 1.5 mol, in particular from about 0.95 to 1.1 mol, of compound of formula (VIII) are employed per mol of the compound (IV).

The reaction of the compound of formula (IV) with a chlorinating agent in the presence of a compound of formula (VIII) can be carried out in water as solvent. Organic solvents suitable for the reaction are protic polar solvents, for example aliphatic alcohols having preferably 1 to 4 carbon atoms, such as methanol, ethanol, n-propanol, isopropanol, n-butanol, isobutanol or tert-butanol, or carboxylic acids, such as acetic acid, aromatic hydrocarbons, such as benzene, toluene, xylenes, cumene, chlorobenzene, nitrobenzene or tert-butylbenzene, aprotic polar solvents, for example cyclic or acyclic ethers, such as diethyl ether, tert-butyl methyl ether (MTBE), tetrahydrofuran (THF) or dioxane, cyclic or acyclic amides, such as dimethylformamide, dimethylacetamide, N-methylpyrrolidone or tetramethylurea, or aliphatic nitriles, such as acetonitrile or propionitrile, and also mixtures of the solvents mentioned above or mixtures of the solvents mentioned above and water.

The reaction is preferably carried out in water or in cyclic or acyclic ethers, such as diethyl ether, tert-butyl methyl ether (MTBE), tetrahydrofuran (THF) or dioxane, cyclic or acyclic amides, such as dimethylformamide, dimethylacetamide, N-methylpyrrolidone or tetramethylurea, or aliphatic nitriles, such as acetonitrile or propionitrile, and also mixtures of the solvents mentioned above or mixtures of the solvents mentioned above and water.

Work-up of the reaction mixture and isolation of the compound of formula (XV) are carried out in a customary manner, for example by removing the solvent, for example by distillation or by aqueous extractive work-up or by a combination of these measures.

Further purification can be carried out, for example, by crystallization or by chromatography. However, frequently, the product is already obtained in a purity which does not require further purification steps.

The reaction mixtures obtained in the reaction of compounds of the formula (IV) with a chlorinating agent in the presence of compounds of formula (VIII) are generally subjected to aqueous work-up, i.e. the reaction mixture obtained is brought into contact with water or an aqueous solution. After neutralization of the water-containing reaction mixtures obtained in this manner, the compounds of the formula (XV) can generally be isolated by extraction with an organic solvent and subsequent removal of the organic solvent. If appropriate, especially when water-miscible solvents are used for the reaction, it may be advantageous to remove at least some of the solvent prior to the extraction, for example by distillation.

Further, in process step A.3, the compound (IV) can be prepared from compound (II) via two different methods:

Method B.1: Compound of Formula (IV) is Prepared Starting from Compound of Formula (II) Via an Intermediate Compound of Formula (III) (Two Step Method)

Step B.1a: Reaction of a compound of the formula (II) to a compound of formula (III)

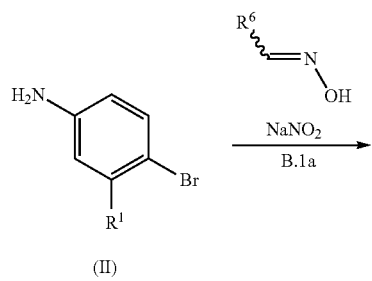

(II)

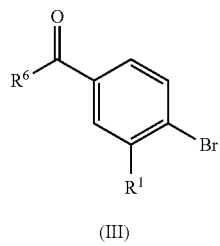

(III)

In this upstream process step for the preparation of compounds of formula (I), the reaction of a compound of the formula (II) takes place with sodium nitrite and formoxime and results in compounds of formula (III), wherein $R^6$ is hydrogen.

The reaction of a compound of the formula (II) with sodium nitrite and formoxime ($R^6$ is H) to compound (III) is preferably carried out at temperatures of from −20 to 120° C. In general, the upper temperature limits the boiling point of the solvent in question when the reaction is carried out under atmospheric pressure.

In the reaction of compounds of the formula (XVI) with sodium nitrite and formoxime the pressure is preferably in a range of from 0.9 to 2 bar, particularly preferably in a range of from 0.9 to 1.5 bar and especially in a range of from 0.9 to 1.1 bar.

The sodium nitrite is preferably employed in a molar ratio of from 0.9 to 2 mol per mol of the compound (II). Preferably, from 0.9 to 1.2 mol, in particular from about 0.95 to 1.1 mol, of sodium nitrite are employed per mol of the compound (II). The formoxime is preferably employed in a molar ratio of from 0.9 to 2 mol per mol of the compound (II). Preferably, from 0.9 to 1.2 mol, in particular from about 0.95 to 1.1 mol, of formoxime are employed per mol of the compound (II).

The reaction of the compound of formula (II) with sodium nitrite and formoxime is generally carried out in water as solvent. Organic solvents suitable for the reaction with formoxime or an aldoxime are protic polar solvents, for example aliphatic alcohols having preferably 1 to 4 carbon atoms, such as methanol, ethanol, n-propanol, isopropanol, n-butanol, isobutanol or tert-butanol, or carboxylic acids, such as acetic acid, aromatic hydrocarbons, such as benzene, toluene, xylenes, cumene, chlorobenzene, nitrobenzene or tert-butylbenzene, aprotic polar solvents, for example cyclic or acyclic ethers, such as diethyl ether, tert-butyl methyl ether (MTBE), tetrahydrofuran (THF) or dioxane, cyclic or acyclic amides, such as dimethylformamide, dimethylacetamide, N-methylpyrrolidone or tetramethylurea, or aliphatic nitriles, such as acetonitrile or propionitrile, and also mixtures of the solvents mentioned above.

The reaction is preferably carried out in water and a protic polar solvent, in particular in a $C_1$-$C_4$-alcohol or a carboxylic acid and particularly preferably in methanol, ethanol, acetonitrile or acetic acid, or in a mixture of a protic polar solvent with an aprotic polar solvent or in a mixture of these solvents with water. The amount of water is preferably more than 30% by volume, in particular more than 50% by volume, based on the total amount of organic solvent+water, and is preferably in the range of from 50 to 100% by volume, in particular in the range of from 60 to 100% by volume, based on the total amount of organic solvent+water.

Work-up of the reaction mixture and isolation of the compound of formula (III) are carried out in a customary manner, for example by removing the solvent, for example by distillation or by aqueous extractive work-up or by a combination of these measures. Further purification can be carried out, for example, by crystallization or by chromatography. However, frequently, the product is already obtained in a purity which does not require further purification steps.

The reaction mixtures obtained in the reaction of compounds of the formula (II) with sodium nitrite are generally subjected to aqueous work-up, i.e. the reaction mixture obtained is brought into contact with water or an aqueous solution. After acidification of the water-containing reaction mixtures obtained in this manner, the compounds of the formula (III) can generally be isolated by extraction with an organic solvent and subsequent removal of the organic solvent. If appropriate, especially when water-miscible solvents are used for the reaction, it may be advantageous to remove at least some of the solvent prior to the extraction, for example by distillation.

The reaction of compounds of formula (II) with sodium nitrite is generally carried out in the presence of aqueous solutions of acids such as hydrochloric acid and sulfuric acid. After obtaining the diazonium solution, sodium acetate is added to adjust the pH value between 1 and 5. Copper sulfate needs to be added to the formoxime solution, before adding the diazonium solution prepared above. The preferred amount of copper sulfate is from 0.001 to 0.2 mol, in particular from about 0.01 to 0.1 mol, of copper sulfate are employed per mol of the compound (II). Sodium sulfite needs to be added to the formoxime or acetaloxime solution, before adding the diazonium solution prepared above. The preferred amount of sodium sulfite is from 0.001 to 0.2 mol, in particular from about 0.01 to 0.1 mol, of sodium sulfite are employed per mol of the compound (II).

The reaction mixture obtained by the reaction of compounds of formula (II) with sodium nitrite and formoxime— is subjected to acidic workup. This involves, for example stirring together with aqueous solutions of acids such as hydrochloric acid, hydrobromic acid or sulfuric acid at temperatures ranging from room temperature to the boiling point of the respective solvent mixture present.

Step B.1b Subsequent Reaction of the Compound of the Formula (III) to Compound of Formula (IV)

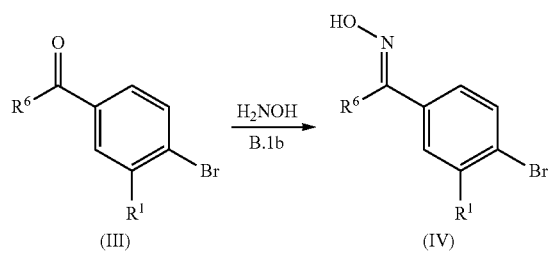

The reaction of a compound of the formula (III) with hydroxylamine to a compound of formula (IV) is preferably carried out at temperatures of from −20 to 120° C. In general, the upper temperature limits the boiling point of the solvent in question when the reaction is carried out under atmospheric pressure.

In the reaction of compounds of the formula (III) with hydroxylamine the pressure is preferably in a range of from 0.9 to 2 bar, particularly preferably in a range of from 0.9 to 1.5 bar and especially in a range of from 0.9 to 1.1 bar.

The hydroxylamine is preferably employed in a molar ratio of from 0.9 to 2 mol per mol of the compound (III). Preferably, from 0.9 to 1.2 mol, in particular from about 0.95 to 1.1 mol, of hydroxylamine are employed per mol of the compound (III).

The reaction of the compound of formula (III) with hydroxylamine can be carried out in water as solvent. Organic solvents suitable for the reaction are protic polar solvents, for example aliphatic alcohols having preferably 1 to 4 carbon atoms, such as methanol, ethanol, n-propanol, isopropanol, n-butanol, isobutanol or tert-butanol, or carboxylic acids, such as acetic acid, aromatic hydrocarbons, such as benzene, toluene, xylenes, cumene, chlorobenzene, nitrobenzene or tert-butylbenzene, aprotic polar solvents, for example cyclic or acyclic ethers, such as diethyl ether, tert-butyl methyl ether (MTBE), tetrahydrofuran (THF) or dioxane, cyclic or acyclic amides, such as dimethylformamide, dimethylacetamide, N-methylpyrrolidone or tetramethylurea, or aliphatic nitriles, such as acetonitrile or propionitrile, and also mixtures of the solvents mentioned above or mixtures of the solvents mentioned above and water.

The reaction is preferably carried out in water or a protic polar solvent, in particular in a $C_1$-$C_4$-alcohol or a carboxylic acid and particularly preferably in methanol, ethanol, acetonitrile or acetic acid, or in a mixture of a protic polar solvent with an aprotic polar solvent or in a mixture of these solvents with water.

Work-up of the reaction mixture and isolation of the compound of formula (IV) are carried out in a customary manner, for example by removing the solvent, for example by distillation or by aqueous extractive work-up or by a combination of these measures. Further purification can be carried out, for example, by crystallization or by chromatography. However, frequently, the product is already obtained in a purity which does not require further purification steps.

The reaction mixtures obtained in the reaction of compounds of the formula (III) with hydroxylamine are generally subjected to aqueous work-up, i.e. the reaction mixture obtained is brought into contact with water or an aqueous solution. After neutralization of the water-containing reaction mixtures obtained in this manner, the compounds of the formula (IV) can generally be isolated by extraction with an organic solvent and subsequent removal of the organic solvent. If appropriate, especially when water-miscible solvents are used for the reaction, it may be advantageous to remove at least some of the solvent prior to the extraction, for example by distillation.

The reaction of compounds of formula (III) with hydroxylamine is generally carried out in the presence of inorganic acids such as hydrochloric acid, sulfuric acid or of an organic acid such as acetic acid, toluene sulfonic acid or benzoic acid. Preferably, the amount of acid employed is in a molar ratio of from 0.001 to 2 mol per mol of the compound (III). Preferably, from 0.01 to 1.2 mol, in particular from about 0.1 to 1.1 mol, of acid are employed per mol of the compound (III). Ideally, the hydroxylamine employed for the reaction is used as the salt of the respective acid, especially as the hydrochloride.

Method B.2: the Compound of Formula (IV) is Prepared Directly from Compound of Formula (II) (One-Step-Method)

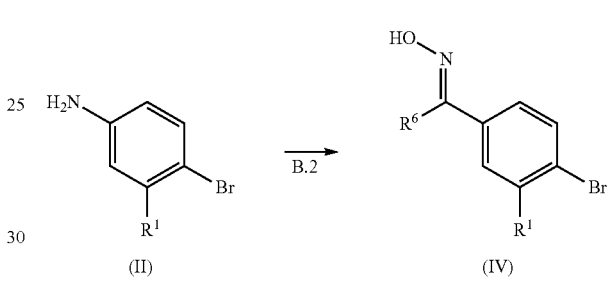

The reaction conditions, applied temperatures, solvents, reactants, catalysts, acids and buffers described above for the method B remain unchanged, except for the workup procedure. For the reaction of compounds of formula (II) to compounds of formula (IV), the aqueous workup is carried out at a pH value between 3 and 12, preferably between 5 and 10 and especially between 5 and 9. Compounds of the formula (IV) can generally be isolated by extraction with an organic solvent and subsequent removal of the organic solvent. If appropriate, especially when water-miscible solvents are used for the reaction, it may be advantageous to remove at least some of the solvent prior to the extraction, for example by distillation.

Furthermore the compound of formula (II) may be prepared by bromination of compounds of formula (IX):

C.1 Upstream Reaction of a Compound of the Formula (IX) to a Compound Of Formula (II)

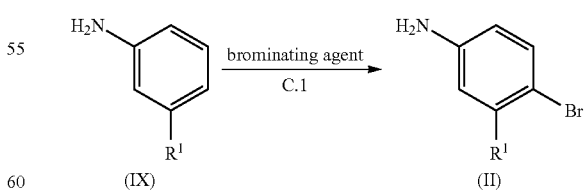

The term brominating agent refers to reagent independently selected from bromine, N-bromsuccinimide, dibromodimethylhydantoine, aqueous $HBr/H_2O_2$, pyridinium hydrobromide, bromine pentafluoroantimonate hydrofluoride, or compounds of the formula (XVII):

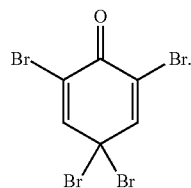

(XVII)

The reaction of a compound of the formula (IX) with a brominating agent is preferably carried out at temperatures of from −20 to 120° C. In general, the upper temperature is limits the boiling point of the solvent in question when the reaction is carried out under atmospheric pressure.

In the reaction of compounds of the formula (IX) with a brominating agent the pressure is preferably in a range of from 0.9 to 100 bar, particularly preferably in a range of from 0.9 to 10 bar and especially in a range of from 0.9 to 3 bar.

The brominating agent is preferably employed in a molar ratio of from 0.9 to 2 mol per mol of the compound (IX). Preferably, from 0.9 to 1.2 mol, in particular from about 0.95 to 1.1 mol, of the brominating agent are employed per mol of the compound (IX).

Organic solvents suitable for the reaction with brominating agents are aprotic solvents, for example dichloromethane, tetrachloromethane, 1,2-dichloroethane, decane, aromatic hydrocarbons, such as benzene, toluene, xylenes, cumene, chlorobenzene, nitrobenzene or tert-butylbenzene, aprotic polar solvents, for example cyclic or acyclic ethers, such as diethyl ether, tert-butyl methyl ether (MTBE), tetrahydrofuran (THF) or dioxane, decane, tetrahydrofuran, toluene, xylenes, cumene, chlorobenzene, nitrobenzene, and dipolar aprotic solvents for example DMF, NMP, DMEU, DMPU, tetraalkylureas, DMSO, sulpholane and also mixtures of the solvents mentioned above.

Work-up of the reaction mixture and isolation of the compound of formula (II) are carried out in a customary manner, for example by removing the solvent, for example by distillation or by aqueous extractive work-up or by a combination of these measures. Further purification can be carried out, for example, by crystallization or by chromatography. However, frequently, the product is already obtained in a purity which does not require further purification steps.

The reaction mixtures obtained in the reaction of compounds of the formula (IX) with a brominating agent are generally subjected to aqueous work-up, i.e. the reaction mixture obtained is brought into contact with water or an aqueous solution. After neutralization of the water-containing reaction mixtures obtained in this manner, the compounds of the formula (II) can generally be isolated by extraction with an organic solvent and subsequent removal of the organic solvent. If appropriate, especially when water-miscible solvents are used for the reaction, it may be advantageous to remove at least some of the solvent prior to the extraction, for example by distillation.

Alternatively to process step A.3, the reaction of of compound of formula (IV) to compound of formula (XV) may also be performed in a two step process.

A.3a A Compound of Formula (IV) is First Reacted to a Compound of the Formula (V)

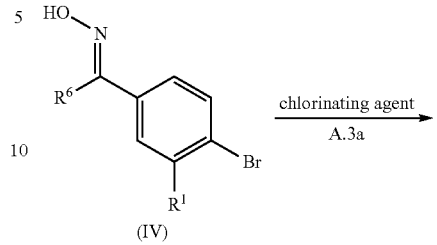

(IV)

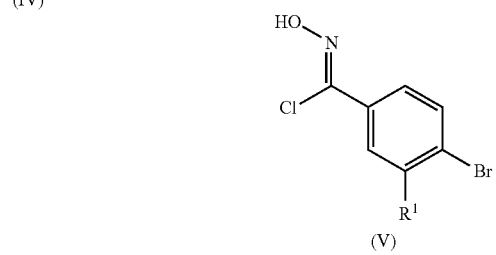

(V)

The term chlorinating agent refers to a reagent independently selected from chlorine, sodium hypochlorite, N-chlorosuccinimide or chloramine T.

The reaction of a compound of the formula (IV) with a chlorinating agent to a compound of formula (V) is preferably carried out at temperatures of from −20 to 140° C. In general, the upper temperature limits the boiling point of the solvent in question when the reaction is carried out under atmospheric pressure.

In the reaction of compounds of the formula (IV) with a chlorinating agent the pressure is preferably in a range of from 0.9 to 2 bar, particularly preferably in a range of from 0.9 to 1.5 bar and especially in a range of from 0.9 to 1.3 bar.

The chlorinating agent is preferably employed in a molar ratio of from 0.9 to 2 mol per mol of the compound (IV). Preferably, from 0.9 to 1.2 mol, in particular from about 0.95 to 1.1 mol, of a chlorinating agent are employed per mol of the compound (IV).

The reaction of the compound of formula (IV) with a chlorinating agent can be carried out in water as solvent. Organic solvents suitable for the reaction are protic polar solvents, for example aliphatic alcohols having preferably 1 to 4 carbon atoms, such as methanol, ethanol, n-propanol, isopropanol, n-butanol, isobutanol or tert-butanol, or carboxylic acids, such as acetic acid, aromatic hydrocarbons, such as benzene, toluene, xylenes, cumene, chlorobenzene, nitrobenzene or tert-butylbenzene, aprotic polar solvents, for example cyclic or acyclic ethers, such as diethyl ether, tert-butyl methyl ether (MTBE), tetrahydrofuran (THF) or dioxane, cyclic or acyclic amides, such as dimethylformamide, dimethylacetamide, N-methylpyrrolidone or tetramethylurea, or aliphatic nitriles, such as acetonitrile or propionitrile, and also mixtures of the solvents mentioned above or mixtures of the solvents mentioned above and water.

The reaction is preferably carried out in cyclic or acyclic ethers, such as diethyl ether, tert-butyl methyl ether (MTBE), tetrahydrofuran (THF) or dioxane, cyclic or acyclic amides, such as dimethylformamide, dimethylacetamide, N-methylpyrrolidone or tetramethylurea, or aliphatic nitriles, such as acetonitrile or propionitrile, and also mixtures of the solvents mentioned above Work-up of the reaction mixture and isolation of the compound of formula (V) are carried out in a customary manner, for example by removing the solvent, for example by distillation or by aqueous extractive work-up or by a combination of these measures.

Further purification can be carried out, for example, by crystallization or by chromatography. However, frequently, the product is already obtained in a purity which does not require further purification steps.

The reaction mixtures obtained in the reaction of compounds of the formula (IV) with a chlorinating agent are generally subjected to aqueous work-up, i.e. the reaction mixture obtained is brought into contact with water or an aqueous solution. After neutralization of the water-containing reaction mixtures obtained in this manner, the compounds of the formula (V) can generally be isolated by extraction with an organic solvent and subsequent removal of the organic solvent. If appropriate, especially when water-miscible solvents are used for the reaction, it may be advantageous to remove at least some of the solvent prior to the extraction, for example by distillation.

Alternatively, reaction mixtures obtained in the reaction of compounds of the formula (IV) with a chlorinating agent can be used as solution for the next transformation without any further workup.

A.3b the Compound of Formula (V) is Secondly Reacted with a Compound of Formula (VIII) to a Compound of the Formula (XV)

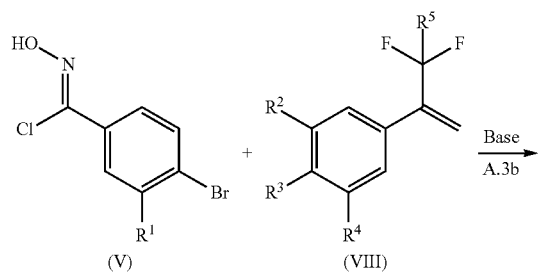

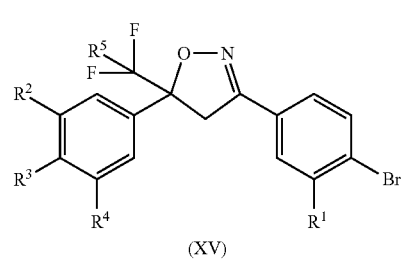

The term base refers to a reagent independently selected from triethylamine, pyridine, potassium carbonate, sodium carbonate, potassium hydrogen carbonate, sodium hydrogen carbonate, or ethyl magnesium bromide. The base is also present in the one step process step A.3).

The reaction of a compound of the formula (V) with a compound of formula (VIII) to a compound of formula (XV) is preferably carried out at temperatures of from −20 to 120° C. In general, the upper temperature limits the boiling point of the solvent in question when the reaction is carried out under atmospheric pressure.

In the reaction of compounds of the formula (V) with a compound of formula (VIII) to a compound of formula (XV) the pressure is preferably in a range of from 0.9 to 2 bar, particularly preferably in a range of from 0.9 to 1.5 bar and especially in a range of from 0.9 to 1.3 bar.

The compounds of the formula (V) is preferably employed in a molar ratio of from 0.5 to 5 mol per mol of the compound (VIII). Preferably, from 0.7 to 2 mol, in particular from about 0.8 to 1.1 mol, of compounds of the formula (V) are employed per mol of the compound (VIII). The reaction is performed in the presence of a suitable base. The base is preferably employed in a molar ratio of from 0.5 to 100 mol per mol of the compound (V). Preferably, from 0.9 to 10 mol, in particular from about 0.95 to 5 mol, of base are employed per mol of the compound of formula (V).

The reaction of the compound of formula (V) with a a compound of formula (VIII) can be carried out in water as solvent. Organic solvents suitable for the reaction are protic polar solvents, for example aliphatic alcohols having preferably 1 to 4 carbon atoms, such as methanol, ethanol, n-propanol, isopropanol, n-butanol, isobutanol, 1,2-ethanediol or tert-butanol, aromatic hydrocarbons, such as benzene, toluene, xylenes, cumene, chlorobenzene, nitrobenzene, pyridine or tert-butylbenzene, aprotic polar solvents, for example cyclic or acyclic ethers, such as diethyl ether, tert-butyl methyl ether (MTBE), tetrahydrofuran (THF), ethyleneglycol dimethylether (DME), or dioxane, cyclic or acyclic amides, such as dimethylformamide, dimethylacetamide, N-methylpyrrolidone or tetramethylurea cyclic or acyclic ester, such as ethyl acetate or gamma butyrolactone, or aliphatic nitriles, such as acetonitrile or propionitrile, or halogenated hydrocarbons, such as dichloromethane, chloroform, tetrachloromethane, 1,2-dichloroethane, 1,1,1-trichloroethane, and also mixtures of the solvents mentioned above or mixtures of the solvents mentioned above and water.

The reaction is preferably carried out in water or in cyclic or acyclic ethers, such as diethyl ether, tert-butyl methyl ether (MTBE), tetrahydrofuran (THF) or dioxane, cyclic or acyclic amides, such as dimethylformamide, dimethylacetamide, N-methylpyrrolidone or tetramethylurea, or aliphatic nitriles, such as acetonitrile or propionitrile, and also mixtures of the solvents mentioned above or mixtures of the solvents mentioned above and water.

Work-up of the reaction mixture and isolation of the compound of formula (XV) are carried out in a customary manner, for example by removing the solvent, for example by distillation or by aqueous extractive work-up or by a combination of these measures. Further purification can be carried out, for example, by crystallization or by chromatography. However, frequently, the product is already obtained in a purity which does not require further purification steps.

The reaction mixtures obtained in the reaction of compounds of the formula (V) with a compound of formula (VIII) are generally subjected to aqueous work-up, i.e. the reaction mixture obtained is brought into contact with water or an aqueous solution. After neutralization of the water-containing reaction mixtures obtained in this manner, the compounds of the formula (XV) can generally be isolated by extraction with an organic solvent and subsequent removal of the organic solvent. If appropriate, especially when water-miscible solvents are used for the reaction, it may be advantageous to remove at least some of the solvent prior to the extraction, for example by distillation.

A.4 Subsequent Reaction of a Compound of the Formula (XV) to a Compound of Formula (I)

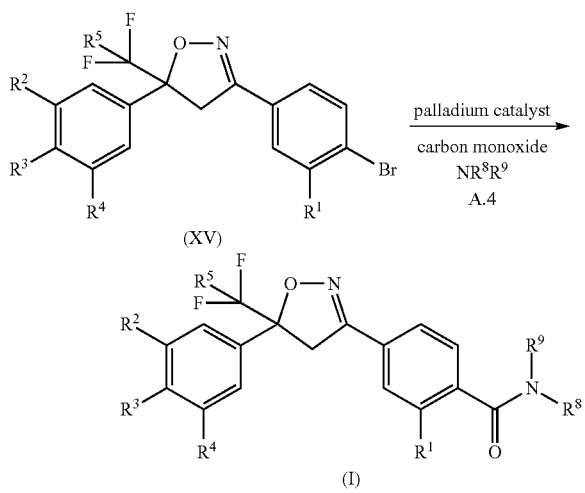

The reaction of a compound of the formula (XV) with carbon monoxide and an amine to a compound of formula (I) is preferably carried out at temperatures of from −20 to 140° C. In general, the upper temperature limits the boiling point of the solvent in question when the reaction is carried out under atmospheric pressure.

In the reaction of compounds of the formula (XV) with carbon monoxide and an amine to a compound of formula (I) the pressure is preferably in a range of from 0.9 to 100 bar, particularly preferably in a range of from 0.9 to 50 bar and especially in a range of from 0.9 to 20 bar.

The amine is preferably employed in a molar ratio of from 0.8 to 5 mol per mol of the compound (XV). Preferably, from 0.9 to 2 mol, in particular from about 0.95 to 1.5 mol, of amine are employed per mol of the compound (XV). The reaction is performed in the presence of a suitable base. The base is preferably employed in a molar ratio of from 0.5 to 100 mol per mol of the compound (XV). Preferably, from 0.9 to 10 mol, in particular from about 0.95 to 5 mol, of base are employed per mol of the compound of formula (V). The reaction is performed in the presence of a suitable catalyst. The catalyst is preferably employed in a molar ratio of from 0.00001 mol to 0.1 mol of the compound (XV). Preferably, from 0.0001 mol to 0.05 mol, of the catalyst are employed per mol of the compound of formula (XV).

Organic solvents suitable for the reaction are protic polar solvents, for example aliphatic alcohols having preferably 1 to 4 carbon atoms, such as methanol, ethanol, n-propanol, isopropanol, n-butanol, isobutanol, 1,2-ethanediol or tert-butanol, aromatic hydrocarbons, such as benzene, toluene, xylenes, cumene, chlorobenzene, nitrobenzene, pyridine or tert-butylbenzene, aprotic polar solvents, for example cyclic or acyclic ethers, such as diethyl ether, tert-butyl methyl ether (MTBE), tetrahydrofuran (THF), ethyleneglycol dimethylether (DME), or dioxane, cyclic or acyclic amides, such as dimethylformamide, dimethylacetamide, N-methylpyrrolidone or tetramethylurea cyclic or acyclic ester, such as ethyl acetate or gamma butyrolactone, or aliphatic nitriles, such as acetonitrile or propionitrile, or halogenated hydrocarbons, such as dichloromethane, chloroform, tetrachloromethane, 1,2-dichloroethane, 1,1,1-trichloroethane, and also mixtures of the solvents mentioned above or mixtures of the solvents mentioned above and water.

The reaction is preferably carried out in cyclic or acyclic ethers, such as diethyl ether, tert-butyl methyl ether (MTBE), tetrahydrofuran (THF) or dioxane, cyclic or acyclic amides, such as dimethylformamide, dimethylacetamide, N-methylpyrrolidone or tetramethylurea, or aliphatic nitriles, such as acetonitrile or propionitrile, aromatic hydrocarbons, such as benzene, toluene, xylenes, cumene, chlorobenzene, nitrobenzene, pyridine or tert-butylbenzene and also mixtures of the solvents mentioned above or mixtures of the solvents mentioned above and water.

Work-up of the reaction mixture and isolation of the compound of formula (I) are carried out in a customary manner, for example by removing the solvent, for example by distillation or by aqueous extractive work-up or by a combination of these measures.

Further purification can be carried out, for example, by crystallization or by chromatography. However, frequently, the product is already obtained in a purity which does not require further purification steps.

The reaction mixtures obtained in the reaction of compounds of the formula (XV) with carbon monoxide and an amine are generally subjected to aqueous work-up, i.e. the reaction mixture obtained is brought into contact with water or an aqueous solution. After neutralization of the water-containing reaction mixtures obtained in this manner, the compounds of the formula (I) can generally be isolated by extraction with an organic solvent and subsequent removal of the organic solvent. If appropriate, especially when water-miscible solvents are used for the reaction, it may be advantageous to remove at least some of the solvent prior to the extraction, for example by distillation.

The term base refers to a reagent independently selected from triethylamine, pyridine, potassium carbonate, sodium carbonate, potassium hydrogen carbonate, or sodium hydrogen carbonate.

Suitable palladium catalysts for the reaction of the compounds of the formula (XV) with amines are palladium-containing compounds in which the palladium has an oxidation state of 0 or 2.

Examples of palladium-containing compounds having an oxidation state of 0 are palladium(0) ligand complexes, such as palladium(0)tetrakis(triphenylphosphine), palladium(0) tetrakis(diphenylmethylphosphine) or palladium(0)-bis (DIPHOS), or metallic palladium which may be supported, if appropriate. Metallic palladium is preferably applied to an inert support, such as activated carbon, alumina, barium sulfate, barium carbonate or calcium carbonate. The reaction in the presence of metallic palladium is preferably carried out in the presence of suitable complex ligands.

Examples of palladium-containing compounds having an oxidation state of 2 are palladium(II) ligand complexes, such as palladium(II) acetylacetonate, or compounds of the formula $PdX_2L_2$ in which X is halogen and L is a monovalent ligand, in particular a ligand of the formula (A) or (B) shown below, and also palladium(II) salts, such as, for example, palladium acetate or palladium chloride, preferably palladium chloride.

If palladium(II) salts are used, the reaction is preferably carried out in the presence of suitable complex ligands, especially in the complex ligands of the formulae (A) and (B) shown below.

The palladium catalyst may be employed in the form of a finished palladium complex or as a palladium compound which, under the reaction conditions, forms, as a pre-catalyst, the catalytically active compound together with suitable ligands.

Suitable complex ligands for the reaction according to the invention of compounds of the formula (XV) with amines are, for example, mono- or bidentate phosphines of the formulae (A) and (B) shown below

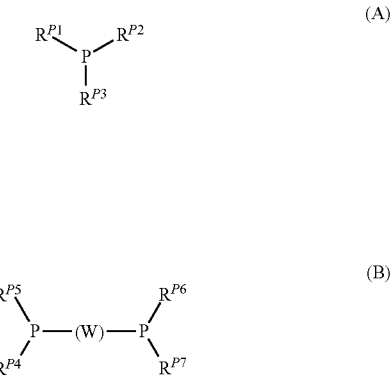

in which $R^{P1}$ to $R^{P7}$ are independently of one another $C_1$-$C_6$-alkyl, $C_5$-$C_8$-cycloalkyl, adamantyl, aryl-$C_1$-$C_2$-alkyl or, preferably, ferrocenyl or aryl which may optionally be substituted by $C_1$-$C_4$-alkyl or $C_1$-$C_4$-alkoxy, and W is a straight-chain bivalent hydrocarbon group having preferably 2 to 5 carbon atoms which is unsubstituted or optionally substituted, where the bivalent hydrocarbon group may be part of a mono- or bicyclic ring which for its part is unsubstituted or may have further substituents.

A in the compounds of the formulae (A) and (B) is especially $C_2$-$C_4$-alkylene, $C_0$-$C_1$-alkyleneferrocenyl, 1,1'-biphenyl-2,2'-diyl or 1,1'-binaphthyl-2,2'-diyl, where the four last-mentioned groups may optionally be substituted by $C_1$-$C_4$-alkyl or $C_1$-$C_4$-alkoxy and where $C_1$-$C_4$-alkylene may additionally have one or more substituents selected from the group consisting of $C_3$-$C_7$-cycloalkyl, aryl and benzyl. In this context, aryl is naphthyl or optionally substituted phenyl. Aryl is preferably phenyl or tolyl, particularly preferably phenyl. $C_0$-$C_1$-Alkyleneferrocenyl is especially ferrocenediyl, where the two phosphorus atoms are in each case attached to one cyclopentadiene of the ferrocene, or is methyleneferrocenyl, where one of the phosphorus atoms is attached via the methylene group to a cyclopentadiene, the second phosphorus atom is attached to the same cyclopentadiene and the methylene group may optionally have 1 or 2 further substituents selected from $C_1$-$C_4$-alkyl.

The complex ligands used in the process according to the invention for reacting compounds of the formula (XV) with amines are preferably bidentate phosphines, such as 1,3-bis(diphenylphosphino)propane (DPPP), 1,3-bis(diphenylphosphino)ethane, 1,3-bis(dicyclohexylphosphino)propane (DCPP), ferrocenyl-containing phosphines of the JosiPhos type, 1,1'-bis(diphenylphosphino)ferrocene (DPPF) or 2,2-dimethyl-1,3-bis(diphenylphosphino)propane and particularly preferably 2,2-dimethyl-1,3-bis(diphenylphosphino)propane.

In the process according to the invention, the palladium catalyst is preferably employed in an amount of from 0.01 to 5 mol %, particularly preferably from 0.1 to 1 mol %, based on the amount of the isoxazoline of the formula (XV) used.

In a preferred embodiment, the process according to the invention for reacting compounds of the formula (XV) with amines is carried out in the presence of an auxiliary base.

Suitable auxiliary bases are, for example, basic alkali metal salts and tertiary amines.

Examples of basic alkali metal salts are potassium phosphate, sodium phosphate, potassium carbonate, sodium carbonate, potassium acetate or sodium acetate. Preferably, the alkali metal salt should be essentially water-free. Particular preference is given to using dry potassium carbonate or potassium phosphate. In this embodiment, alkali metal salts are preferably employed in an amount of at least one, particularly preferably 1 to 4 and especially about 2 molar equivalents, based on the amount of the isoxazoline compound of the formula (XV) used.

Suitable tertiary amines are, for example, tri($C_1$-$C_6$-alkyl)amines, such as trimethylamine, triethylamine or diisopropylethylamine, N-methylpiperidine, pyridine, substituted pyridines, such as 2,4,6-trimethylpyridine (collidine), 2,6-dimethylpyridine (lutidine), 2-methylpyridine, (α-picoline), 3-methylpyridine (β-picoline), 4-methylpyridine (γ-picoline) and 4-dimethylaminopyridine, and also bicyclic amines, such as 1,4-diazabicyclo[2.2.2]octane, 1,8-diazabicyclo[5.4.0]undec-7-ene or 1,5-diazabicyclo[4.3.0]non-5-ene. Particular preference is given to using triethylamine, pyridine or 1,8-diazabicyclo[5.4.0]undec-7-ene. Tertiary amines may be employed in an amount of from 0.1 to 4 molar equivalents, based on the amount of the isoxazoline compound of the formula (XV) used.

In a preferred embodiment of the process according to the invention, the reaction of a compound of the formula (XV) with an amine is carried out in the presence of at least one tertiary amine and at least one alkali metal salt.

In this embodiment, the alkali metal salt is preferably employed in an amount of from 1 to 4 and especially about 2 molar equivalents, based on the amount of the isoxazoline compound of the formula (XV) used. In this embodiment, the tertiary amine is preferably employed in an amount of from 0.1 to 4, preferably from 0.2 to 0.7, molar equivalents, based on the amount of the isoxazoline compound of the formula (XV) used.

In this embodiment, the auxiliary base is preferably employed in a total amount of from 2 to 5 molar equivalents, based on the amount of the isoxazoline compound of the formula (XV) used.

The solvent used is preferably essentially water-free, i.e. the solvent has a water content of less than 1000 ppm and in particular not more than 100 ppm.

EXAMPLES

Hereinbelow, the preparation of substituted isoxazoline and their precursors is illustrated by examples.

The compounds can be characterize e.g. by coupled High Performance Liquid Chromatography/mass spectrometry (HPLC/MS), by $^1$H-NMR and/or by their melting points.

Analytical HPLC column: RP-18 column Chromolith Speed ROD from Merck KgaA, Germany). Elution: acetonitrile+0.1% trifluoroacetic acid (TFA)/water+0.1% trifluoroacetic acid (TFA) in a ratio of from 5:95 to 95:5 in 5 minutes at 40° C.

$^1$H-NMR. The signals are characterized by chemical shift (ppm) vs. tetramethylsilane, by their multiplicity and by their integral (relative number of hydrogen atoms given). The following abbreviations are used to characterize the multiplicity of the signals: m=multiplett, q=quartett, t=triplett, d=doublet and s=singulett.

TABLE C.1

Compound examples (Comp. ex.)

| Comp. ex. no. | Structure |
|---|---|
| 1 | 4-bromo-3-methylbenzaldehyde O-methyl oxime |
| 2 | 1-(3,5-dichlorophenyl)-2,2,2-trifluoroethanone |
| 3 | 1,3-dichloro-5-(3,3,3-trifluoroprop-1-en-2-yl)benzene |
| 4 | 3-(4-bromo-3-methylphenyl)-5-(3,5-dichlorophenyl)-5-(trifluoromethyl)-4,5-dihydroisoxazole |
| 5 | 4-[5-(3,5-dichlorophenyl)-5-(trifluoromethyl)-4,5-dihydroisoxazol-3-yl]-2-methyl-N-(pyridin-2-ylmethyl)benzamide |
| 6 | 3-chloro-4-bromobenzaldehyde O-methyl oxime |
| 7 | 2-bromo-5-[(methoxyimino)methyl]benzonitrile |

TABLE C.1-continued

Compound examples (Comp. ex.)

| Comp. ex. no. | Structure |
|---|---|
| 8 | 1-(3,4,5-trichlorophenyl)-2,2,2-trifluoroethanone |
| 9 | 1-(3-chlorophenyl)-2,2,2-trifluoroethanone |
| 10 | 1-[3-(trifluoromethyl)phenyl]-2,2,2-trifluoroethanone |
| 11 | 1-(trifluoromethyl)-3-(3,3,3-trifluoroprop-1-en-2-yl)benzene |
| 12 | 1-[3,5-bis(trifluoromethyl)phenyl]-2,2,2-trifluoroethanone |
| 13 | 1,2,3-trichloro-5-(3,3,3-trifluoroprop-1-en-2-yl)benzene |
| 14 | 1-chloro-3-(3,3,3-trifluoroprop-1-en-2-yl)benzene |
| 15 | 1,3-bis(trifluoromethyl)-5-(3,3,3-trifluoroprop-1-en-2-yl)benzene |

TABLE C.1-continued

Compound examples (Comp. ex.)

| Comp. ex. no. | Structure |
|---|---|
| 16 | 3,5-dichlorophenyl-5-(trifluoromethyl)-3-(4-bromo-3-chlorophenyl)-4,5-dihydroisoxazole |
| 17 | 3-chlorophenyl-5-(trifluoromethyl)-3-(4-bromo-3-methylphenyl)-4,5-dihydroisoxazole |
| 18 | 3,5-bis(trifluoromethyl)phenyl-5-(trifluoromethyl)-3-(4-bromo-3-methylphenyl)-4,5-dihydroisoxazole |
| 19 | 3-(trifluoromethyl)phenyl-5-(trifluoromethyl)-3-(4-bromo-3-methylphenyl)-4,5-dihydroisoxazole |
| 20 | 3,4,5-trichlorophenyl-5-(trifluoromethyl)-3-(4-bromo-3-methylphenyl)-4,5-dihydroisoxazole |
| 21 | 1-(3,5-dichlorophenyl)-2,2-difluoroethanone |
| 22 | 1-(3,5-dichlorophenyl)-1-(1,1-difluoroethyl... vinyl) compound |

Synthesis Examples

Example S.1

Synthesis of 4-Bromo-3-methyl-benzaldehyde oxime (Compound Example No. 1 of Table C.1)

Preparation of solution A: To a solution of paraformaldehyde (2.40 g, 52.1 mmol) in water (36 mL) was added hydroxylamine hydrochloride (5.600 g, 80.59 mmol). This mixture was heated until a clear solution was obtained (90° C. bath temperature). After cooling, at room temperature NaOAc (10.7 g) were added and the mixture was heated to reflux for another 15 min. (Solution A)

Preparation of solution B: A mixture of 4-bromo-3-methylaniline (9.300 g, 49.99 mmol) in 10% HCl (70 mL) was heated and then cooled to 0-5° C. A solution of NaNO$_2$ (3.500 g, 50.72 mmol) in water (10 mL) was added dropwise. After completion of the addition the solution was stirred for another 15 min at this temperature, when a solution of NaOAc (5.0 g) in water (10 mL) was added.

Sandmeyer reaction: Solution A was placed in a three necked flask with mechanical stirring. Sequentially, CuSO$_4$ (1.35 g, 5.41 mmol), NaSO$_3$ (0.210 g, 1.67 mmol) and NaOAc (34.5 g) were added. To this mixture solution B was added at 10-15° C. and stirred for 1 h. The mixture was extracted with CH$_2$Cl$_2$ and washed with NH$_4$Cl to give a crude product that was chromatographed on SiO$_2$ with C$_6$H$_{12}$/CH$_2$Cl$_2$ to yield the title compound (6.87 g, 64%) as a solid.

HPLC-MS: 2.925 min, M=213.8

$^1$H-NMR (360 MHz, DMSO): δ=2.35 (s, 3H), 7.34 (m, 1H), 7.60 (m, 2H), 8.10 (s, 1H), 11.33 (s, 1H) ppm.

Example S.2

Synthesis of 4-Bromo-3-methyl-benzaldehyde oxime (Compound Example No. 1 of Table C.1)

Preparation of solution A: To a solution of paraformaldehyde (12.0 g, 260 mmol) in water (180 mL) was added hydroxylamine hydrochloride (28.00 g, 253.6 mmol). This mixture was heated until a clear solution was obtained (90° C. bath temperature). After cooling, at room temperature NaOAc (53.5 g) were added and the mixture was heated to reflux for another 15 min. (Solution A)

Preparation of solution B: A mixture of 4-bromo-3-methylaniline (46.50 g, 249.9 mmol) in 10% HCl (350 mL) was heated and then cooled to 0-5° C. A solution of NaNO$_2$ (17.5 g, 253.6 mmol) in water (50 mL) was added dropwise. After completion of the addition the solution was stirred for another 15 min at this temperature, when a solution of NaOAc (25.0 g) in water (50 mL) was added.

Sandmeyer reaction: Solution A was placed in a 3 L three necked flask with mechanical stirring. Sequentially, $CuSO_4$ (6.75 g, 27.1 mmol), $NaSO_3$ (1.05 g, 8.33 mmol) and NaOAc (173 g) were added. To this mixture solution B was added at 10-15° C. After the addition of ⅓ of solution B, MeOH (400 mL) was added, before the remainder was added. Stirring was continued for 2 h at room temperature. The mixture was extracted with $CH_2Cl_2$ and washed with $NH_4Cl$ to give a crude product that contained 61.6% of the title compound based on GC analysis. Chromatography on $SiO_2$ with $C_6H_{12}$/$CH_2Cl_2$ yielded the title compound as a solid.

HPLC-MS: 2.925 min, M=213.8

$^1$H-NMR (360 MHz, DMSO): δ=2.35 (s, 3H), 7.34 (m, 1H), 7.60 (m, 2H), 8.10 (s, 1H), 11.33 (s, 1H) ppm.

Example S.3

Synthesis of 3,5-dichloro-2,2,2-trifluoro acetophenone (Compound Example No. 2 of Table C.1)

To 5.1 g (0.209 mol) Magnesium turnings was added 0.45 g of a 1 molar solution of DIBAL in hexane at 60° C. After 15 min, 3,5-dichloro-bromobenzene (5.0 g, 0.022 mol) and 25 mL THF were added and the mixture was stirred. After start up of the reaction a mixture of 45 g (0.2 mol) 3,5-dichloro-bromobenzene and 250 mL THF was added under reflux. After completion of the reaction the mixture was cooled to 0° C. and 31.1 g (0.219 mol) ethyl trifluoroacetate was added. After 2 h an aqueous solution of $NH_4Cl$ was added an the mixture was separated between MTBE and aqueous $NH_4Cl$ solution. The organic layer was separated and the solvent was removed in vacuum. (34.3 g brown oil; purity 70% acc. to g.c.; yield 50%)

$^1$H-NMR (360 MHz, CDCl$_3$): δ=7.7 (s, 1H), 7.9 (s, 2H) ppm.

In the manner described different electrophiles were used:
Trifluoroacetyl chloride: Yield: 36%
Trifluoroacetyl fluoride: Yield: 10%
N,O-dimethylhydroxyl-amid of trifluoro acetic acid: Yield: 26%.

Example S.4

Synthesis of 1,3-dichloro-5-(1-trifluoromethyl-vinyl)-benzene (Compound Example No. 3 of Table C.1)

To a suspension of methyl-triphenylphosphonium iodide in THF was added KOtBu (0.620 g, 5.54 mmol) at room temperature. After 30 min, 3,5-dichloro-2,2,2-trifluoro acetophenone (1.20 g, 4.94 mmol) was added and the mixture was stirred over night. The mixture was separated between MTBE and aqueous $NH_4Cl$ solution. The organic layer was separated and the solvent was removed in vacuum. Column chromatography on $SiO_2$ with cyclohexane gave the title compound (0.73 g, 61%).

$^1$H-NMR (360 MHz, CDCl$_3$): δ=5.82 (s, 1H), 6.06 (s, 1H), 7.32 (s, 2H), 7.38 (s, 1H) ppm.

Example S.5

Synthesis of 1,3-dichloro-5-(1-trifluoromethyl-vinyl)-benzene (Compound Example No. 3 of Table C.1)

To a suspension of methyl-triphenylphosphonium iodide (161.7 g, 0.450 mol) and 3,5-dichloro-2,2,2-trifluoro acetophenone (100 g, 0.390 mol) in THF (650 mL) was added a solution of KOtBu (55.4 g, 0.490 mol) in THF (280 mL) at 20-25° C. within 20 min. After 1.5 h at room temp, the mixture was separated between heptane and water. The organic layer was washed with 1% aqueous NaCl solution, then the solvent was removed in vacuum. The residue was triturated in n-heptane and filtered over a plug of silica. The filtrate was evaporated to give the title compound (69.00 g, 73%) as an oil (purity 95% acc. to g.c).

$^1$H-NMR (360 MHz, CDCl$_3$): δ=5.82 (s, 1H), 6.06 (s, 1H), 7.32 (s, 2H), 7.38 (s, 1H) ppm.

Example S.5.1.

Synthesis of 1,3-dichloro-5-(1-trifluoromethyl-vinyl)-benzene (Compound Example No. 3 of Table C.1)

To a suspension of methyl-triphenylphosphonium bromide (1637.4 g, 4.50 mol) and 3,5-dichloro-2,2,2-trifluoro acetophenone (941 g, 3.90 mol) in THF (9000 mL) was added a solution of KOtBu (554.7 g, 4.90 mol) in THF (4500 mL) at 18-19° C. within 3 h. After 5 h at room temp, 7500 mL solvent was distilled off under reduced pressure at 48° C., 400 mbar. N-heptane (5000 mL) was added to the reaction mixture and cooled to 10° C. The precipitate was filtered off and the filter cake was washed with 4000 mL n-heptane. The filtrate was evaporated to give the title compound. After distillation the product was obtained (620.00 g, 66%) as an oil (purity 99% acc. to g.c).

Example S.5.2.

Synthesis of 1,3-dichloro-5-(1-trifluoromethyl-vinyl)-benzene (Compound Example No. 3 of Table C.1)

To a suspension of methyl-triphenylphosphonium bromide (11.3 g, 0.03 mol) and 3,5-dichloro-2,2,2-trifluoro acetophenone (10 g, (purity 65%) 0.026 mol) in THF (97 mL) was added a suspension of KOMe (2.49 g, 0.033 mol) in THF (55 mL) at 18-20° C. within 15 min. After 5 h at room temp, 76 mL solvent was distilled off under reduced pressure 48° C., 400 mbar. N-heptane 100 mL was added to the reaction mixture and cooled to 10° C. The precipitate was filtered off and the filter cake was washed with 100 mL of n-heptane. The filtrate was evaporated to give the title compound, (10.8 g, 80%) as an oil (purity 47% acc. to g.c).

Example S.5.3.

Synthesis of 1,3-dichloro-5-(1-trifluoromethyl-vinyl)-benzene (Compound Example No. 3 of Table C.1)

To a suspension of methyl-triphenylphosphonium chloride (9.9 g, 0.03 mol) and 3,5-dichloro-2,2,2-trifluoro acetophenone (10.0 g, purity 65%, 0.026 mol) in THF (97 mL) was added a suspension of KOMe (2.49 g, 0.033 mol) in THF (55 mL) at 18-20° C. within 15 min. After 5 h at 50° C., 76 mL solvent was distilled off under reduced pressure 48° C., 400 mbar. N-heptane 100 mL was added to the reaction mixture and cooled to 10° C. The precipitate was filtered off and the filter cake was washed with 100 mL of n-heptane. The filtrate was evaporated to give the title compound, (10.2 g, 71%) as an oil (purity 45% acc. to g.c).

Example S.5.4

Synthesis of
1,3-dichloro-5-(1-trifluoromethyl-vinyl)-benzene
(Compound Example No. 3 of Table C.1)

To a suspension of methyl-triphenylphosphonium bromide (10.51 g) and 3,5-dichloro-2,2,2-trifluoro acetophenone (10.0 g, purity 65%) in THF (35 mL) was added a suspension of NaOMe (1.73 g) in THF (35 mL) at 20° C. After 1.5 h at room temp and 30 min at 50° C., the reaction was complete by GC. N-heptane 100 mL was added to the reaction mixture and cooled to 10° C. The precipitate was filtered off and the filter cake was washed with 100 mL of n-heptane. The filtrate was evaporated to give the title compound, (9.35 g, 74%) as an oil (purity 51% acc. to g.c).

$^1$H-NMR (360 MHz, CDCl$_3$): δ=5.82 (s, 1H), 6.06 (s, 1H), 7.32 (s, 2H), 7.38 (s, 1H) ppm.

Example S.6

Synthesis of 3-(4-Bromo-3-methyl-phenyl)-5-(3,5-dichloro-phenyl)-5-trifluoromethyl-4,5-dihydro-isoxazole (Compound Example No. 4 of Table C.1)

To a solution of 4-Bromo-3-methyl-benzaldehyde oxime (2.600 g, 12.15 mmol) in DMF (40 mL) was added N-chloro succinimide (1.700 g, 12.73 mmol) and the mixture was heated at 70° C. (bath temperature) for 1 h. After cooling to 0° C., a solution of 1,3-dichloro-5-(1-trifluoromethyl-vinyl)-benzene (2.900 g, 12.03 mmol) in DMF (8 mL), followed by triethylamine (2.00 g, 2.75 mL, 19.8 mmol) was added. After 1 h at this temperature, the cooling bath was removed and the mixture was stirred over night. The mixture was separated between MTBE and aqueous NH$_4$Cl solution. The organic layer was separated and the solvent was removed in vacuum. Column chromatography on SiO$_2$ with heptane/CH$_2$Cl$_2$ gave the title compound (2.95 g, 54%).

HPLC-MS (long method): 4.248 min, M=452.05

Example S.7

Synthesis of 3-(4-Bromo-3-methyl-phenyl)-5-(3,5-dichloro-phenyl)-5-trifluoromethyl-4,5-dihydro-isoxazole (Compound Example No. 4 of Table C.1)

To a solution of 4-Bromo-3-methyl-benzaldehyde oxime (11.13 g, 52.00 mmol) in DMF (50 mL) was added N-chloro succinimide (7.29 g, 54.6 mmol) and the mixture was heated at 75° C. (bath temperature) for 1 h. After cooling, ice-water was added and the mixture was extracted with MTBE. The combined organic layers were sequentially washed with water and brine, dried over Na$_2$SO$_4$ and evaporated. The residue was dissolved in THF (50 mL) and added to a suspension of 1,3-dichloro-5-(1-trifluoro-methyl-vinyl)-benzene (15.60 g, 51.78 mmol) and KHCO$_3$ (9.63 g, 96.2 mmol) in THF (25 mL). The resulting mixture was heated at reflux temperature for 20 h. After cooling, water was added and the mixture was extracted with EtOAc. The combined organic layers were dried and the solvent was removed in vacuum. Column chromatography on SiO$_2$ with heptane/CH$_2$Cl$_2$ gave the title compound (20.00 g, 85%).

HPLC-MS (long method): 4.248 min, M=452.05

Example S.8

Synthesis of 4-[5-(3,5-Dichloro-phenyl)-5-trifluoromethyl-4,5-dihydro-isoxazol-3-yl]-2-methyl-N-pyridin-2-ylmethyl-benzamide (Compound Example No. 5 of Table C.1)

A mixture of 3-(4-Bromo-3-methyl-phenyl)-5-(3,5-dichloro-phenyl)-5-trifluoromethyl-4,5-dihydro-isoxazole (1.02 g, 2.24 mmol), 2-picolylamine (369 mg, 3.41 mmol), Pd(dppf)Cl$_2$ (92 mg, 0.13 mmol) triethylamine (5.2 mL, 3.8 g. 37 mmol) and DMF (50 mL) was flushed with carbon monoxide and stirred under an atmosphere of CO at 100° C. for 26 h. The solvent was removed in vacuum and the residue was taken up in EtOAc, filtered and evaporated. The residue was chromatographed on SiO$_2$ to give the title compound (391 mg, 34%).

HPLC-MS: 3.414 min, M=508.10

Example S.9

Synthesis of 4-Bromo-3-chloro-benzaldehyde oxime (Compound Example No. 6 of Table C.1)

Preparation of solution A: To a solution of paraformaldehyde (37.81 g, 1.26 mol) in water (550 mL) was added hydroxylamine hydrochloride (135.5 g, 1.95 mol). This mixture was heated until a clear solution was obtained (90° C. bath temperature). After cooling, at room temperature NaOAc (260 g) were added. (Solution A)

Preparation of solution B: A mixture of 4-bromo-3-chloroaniline (250 g, 1.21 mol), concentrated hydrochloric acid (422 g) and concentrated sulfuric acid (171 g) in water (550 mL) was cooled to 0-5° C. A solution of NaNO$_2$ (86.88 g, 1.26 mol) in water (200 mL) was added dropwise. After completion of the addition the solution was stirred for another 60 min at this temperature.

Sandmeyer reaction: Solution A was placed in a three necked flask with mechanical stirring. Sequentially, CuSO$_4$ (33.25 g, 0.13 mol), NaSO$_3$ (4.58 g, 0.04 mol) and NaOAc (400 g) were added. To this mixture solution B was added at 0-10° C., after approximately 50% addition time, another 160 g of NaOAc and water (800 mL) was added. The mixture was extracted with CH$_2$Cl$_2$ and washed with NH$_4$Cl to give a crude product that was chromatographed on SiO$_2$ with C$_6$H$_{12}$/CH$_2$Cl$_2$ to yield the title compound (90.7 g, 32%) as a solid.

HPLC-MS: 3.072 min, M=235.70

Example S.10

Synthesis of 4-Bromo-3-cyano-benzaldehyde oxime (Compound Example No. 7 of Table C.1)

Preparation of solution A: To a solution of paraformaldehyde (7.92 g, 0.26 mol) in water (180 mL) was added hydroxylamine hydrochloride (28.39 g, 0.41 mol). This mixture was heated until a clear solution was obtained (90° C. bath temperature). After cooling, at room temperature NaOAc (53.5 g) were added. (Solution A)

Preparation of solution B: A mixture of 4-bromo-3-cyanoaniline (50 g, 0.25 mol), concentrated hydrochloric acid (91 g) and concentrated sulfuric acid (37 g) in water (130 mL) was cooled to 0-5° C. A solution of NaNO$_2$ (18.21 g, 0.26 mol) in water (30 mL) was added dropwise. After completion of the addition the solution was stirred for another 60 min at this temperature.

Sandmeyer reaction: Solution A was placed in a three necked flask with mechanical stirring. Sequentially, CuSO$_4$ (6.04 g, 0.02 mol), NaSO$_3$ (0.9 g, 0.01 mol) and NaOAc (2 g) were added. To this mixture solution B was added at 5-10° C., the pH was adjusted to 3-4 by the addition of further NaOAc during the addition of solution B. After completion of the reaction the mixture was extracted with CH$_2$Cl$_2$ and washed with NH$_4$Cl to give a crude product that was chromatographed on SiO$_2$ with C$_6$H$_{12}$/CH$_2$Cl$_2$ to yield the title compound (17.5 g, 31%) as a solid.

HPLC-MS: 2.476 min, M=226.95

Example S.11

Synthesis of 1,3-dichloro-5-(1-trifluoromethyl-vinyl)-benzene (Compound Example No. 3 of Table C.1)

To a suspension of methyl-triphenylphosphonium bromide (16.17 g, 25.27 mmol) and 3,5-dichloro-2,2,2-trifluoro acetophenone (10.0 g, 41.15 mmol) in THF (65 mL) was added KOtBu (5.54 g, 49.38 mmol) in THF (28 mL) at 20-25° C. After 1.5 h at room temp, the reaction was complete by GC. The mixture was separated between n-heptane and water. The organic layer was separated, washed with brine and the solvent was removed in vacuum. After cooling, the mixture was filtered from precipitating triphenylphosphine oxide to yield the title compound (8.78 g, 79%).

$^1$H-NMR (360 MHz, CDCl$_3$): δ=5.82 (s, 1H), 6.06 (s, 1H), 7.32 (s, 2H), 7.38 (s, 1H) ppm.

Example S.12

Synthesis of 3-(4-Bromo-3-methyl-phenyl)-5-(3,5-dichloro-phenyl)-5-trifluoromethyl-4,5-dihydro-isoxazole (Compound Example No. 4 of Table C.1)

Chlorine gas was bubbled through a suspension of 4-Bromo-3-methyl-benzaldehyde oxime (4.00 g) in ethyl acetate (30 mL) for 1 h. The temperature during the reaction did rise to 40° C. After this time, nitrogen was bubbled through the mixture to remove residual chlorine gas. Then, 1,3-dichloro-5-(1-trifluoro-methyl-vinyl)-benzene (4.26 g) was added and triethylamine (6.9 mL, 5.0 g) in ethyl acetate (15 mL) was added dropwise and the mixture was stirred at room temperature over night. After that, aqueous NaHCO$_3$ solution (10%) was added, and the organic layer was extracted with ethyl acetate. The combined organic layers were dried and the solvent was removed in vacuum. Column chromatography on SiO$_2$ with heptane/CH$_2$Cl$_2$ gave the title compound (4.96 g, 65%).

HPLC-MS (long method): 4.248 min, M=452.05

Example S.13

Synthesis of 3-(4-Bromo-3-chloro-phenyl)-5-(3,5-dichloro-phenyl)-5-trifluoromethyl-4,5-dihydro-isoxazole (Compound Example No. 16 of Table C.1)

To a solution of 4-Bromo-3-chloro-benzaldehyde oxime (95.5 g) in DMF (450 mL) was added N-chloro succinimide (48.54 g) and the mixture was heated at 80° C. (bath temperature) for 1 h. After cooling, the mixture was concentrated to ⅓ of the original volume, ice-water was added and the mixture was extracted three times with MTBE. The combined organic layers were sequentially washed with water and brine, dried over Na$_2$SO$_4$ and evaporated. The residue was dissolved in THF (300 mL) and added to a suspension of 1,3-dichloro-5-(1-trifluoro-methyl-vinyl)-benzene (86.92 g) and KHCO$_3$ (64.1 g) in THF (600 mL). The resulting mixture was heated at reflux temperature for 20 h. After cooling, water was added and the mixture was extracted with EtOAc. The combined organic layers were dried and the solvent was removed in vacuum. The crude product was triturated with cold diisopropyl ether to yield the title compound (114.1 g, 70%) as a colorless solid. The mother liquid contained 55.4 g of a product mixture containing further amounts of the title compound.

HPLC-MS (long method): 4.233 min, M=473.80

Example S.14

Synthesis of 3-(4-Bromo-3-methyl-phenyl)-5-(3,5-dichloro-phenyl)-5-trifluoromethyl-4,5-dihydro-isoxazole (Compound Example No. 4 of Table C.1)

To a solution of 4-Bromo-3-methyl-benzaldehyde oxime (97.00 g, purity 90% acc. to GC) in DMF (450 mL) was added N-chloro succinimide (57.18 g) and the mixture was heated at 80° C. (bath temperature) for 1 h. After cooling, ice-water was added and the mixture was extracted with MTBE. The combined organic layers were sequentially washed with water and brine, dried over Na$_2$SO$_4$ and evaporated. The residue was dissolved in THF (300 mL) and added to a suspension of 1,3-dichloro-5-(1-trifluoro-methyl-vinyl)-benzene (102.40 g) and KHCO$_3$ (75.52 g) in THF (600 mL). The resulting mixture was heated at reflux temperature for 20 h. After cooling, water was added and the mixture was extracted with EtOAc. The combined organic layers were washed with 2 M HCl, and water, dried and the solvent was removed in vacuum. The residue was triturated with cold diisopropyl ether to yield the title compound (124.3 g) as a solid. From the mother liquid, further amounts of the title compound (29.6 g) were collected after concentration and precipitation with n-heptane. Total yield 153.90 g, 83%.

HPLC-MS (long method): 4.248 min, M=452.05

Example S.15

Synthesis of 1,3-dichloro-5-(1-difluoromethyl-vinyl)-benzene (Compound Example No. 22 of Table C.1)

To a suspension of methyl-triphenylphosphonium bromide (1.75 g) and 3,5-dichloro-2,2-difluoro acetophenone (1.0 g) in THF (6.5 mL) was added KOtBu (0.60 g) in THF (2.8 mL) at 20-25° C. After 1.5 h at room temp, the reaction was complete by GC. The mixture was separated between n-heptane and water. The organic layer was separated, washed with brine and the solvent was removed in vacuum. After cooling, the mixture was taken up in n-heptane and filtered over a plug of silica gel. After evaporation of the solvent the title compound (0.58 g, 58%) was obtained as an oil (purity 98.9% acc. to g.c).

$^1$H-NMR (360 MHz, CDCl$_3$): δ=5.76 (m, 2H), 6.32 (t, 1H), 7.38 (m, 3H) ppm.

The invention claimed is:

1. A process for preparing a compound of the formula (I)

(I)

wherein
R¹ is H, $CH_3$, $CF_3$, $CH_2CH_3$, $CH_2CF_3$, Cl, or CN;
R² is H, F, Cl, or $CF_3$;
R³ is H, F, or Cl;
R⁴ is H, F, Cl, or $CF_3$;
R⁵ is H, F, Cl or $CF_3$;
R⁸ is Z-A,
 wherein
 Z is $CH_2$ or $CH_2CH_2$ and
 A is selected from the group consisting of A-1, A-2, A-3, A-4, A-5, A-6, A-7, A-8, A-9, A-10, A-11, A-12, A-13, A-14, A-15, A-16, A-17, A-18, A-19, A-20, A-21

-continued

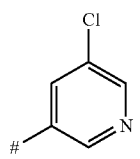 A-22

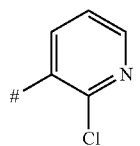 A-23

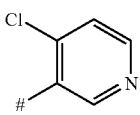 A-24

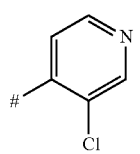 A-25

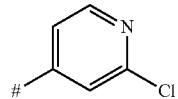 A-26

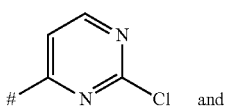 A-27

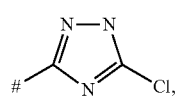 A-28 wherein the "#" in the formulae of variables A indicate the bond to Z;
and
$R^9$ is H, $CH_3$, $CH_2CH_3$, or $CH_2CH_2CH_3$;
comprising A.3: reacting a compound of the formula (VIII) with a compound of formula (IV) in the presence a chlorinating agent selected from the group consisting of chlorine, sodium hypochlorite, N-chlorosuccinimide and chloramine T,
and a base at a temperature from −20 to 120° C. in water or in a solvent selected from the group consisting of cyclic ethers, acyclic ethers, cyclic amides, acyclic amides and aliphatic nitriles, or in mixtures of these solvents, or in mixtures of these solvents and water, to form a compound of formula (XV)

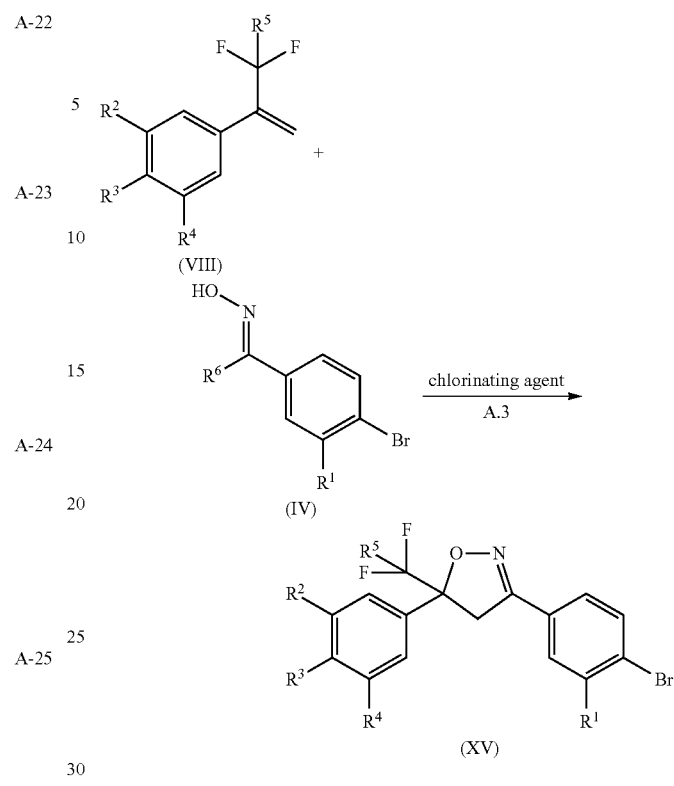

wherein
$R^6$ is H;

A.4: reacting the compound of the formula (XV) with carbon monoxide and an amine in presence of a palladium catalyst, in which the palladium has an oxidation state of 0 or 2, at a temperature from −20 to 140° C. and a pressure from 0.9 to 100 bar in a solvent selected from the group consisting of aliphatic alcohols having 1 to 4 carbon atoms, aromatic hydrocarbons, cyclic or acyclic ethers, cyclic or acyclic amides, cyclic or acyclic esters, aliphatic nitriles, halogenated hydrocarbons, mixtures of the solvents mentioned above and mixtures of the solvents mentioned above and water to form a compound of formula (I)

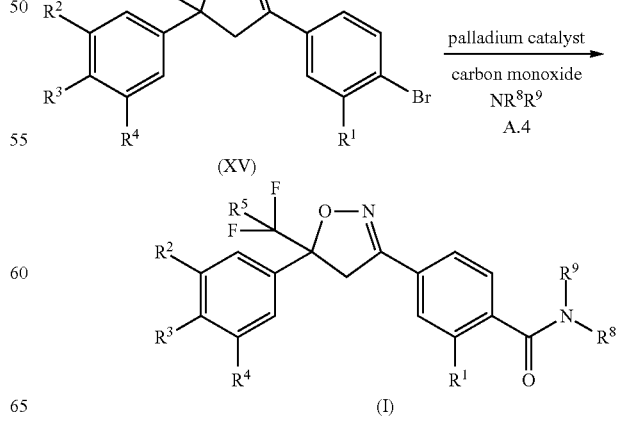

wherein the compound of formula (VIII) is obtained by
A.2: reacting a compound of formula (VII)

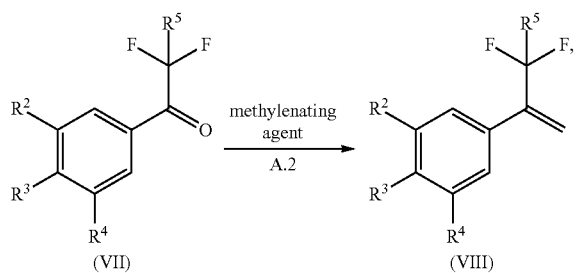

with a methylenating agent to form a compound of formula (VIII), wherein said methylenating agent is selected from the group consisting of dimethyltitanocene, diphenylmethylphosphine oxide, dimethoxymethylphosphine sulfide, pentamethylphosphonic diamide, dimethyl sulfoxide, (trialkylstannyl)(trimethylsilyl)methane, trimethylsilyl(phenylthio)methane, titanium tetrachloride and diiodomethane or dibromomethane, dichlorotitanocene and aluminum trimethyl, methylenetriphenylphosphine, trimethylsulfonium iodide, dichloro(cyclopentadienyl)zirconium and diiodomethane or dibromomethane dimethyl methanephosphonate, methanesulfonyl chloride, (chloromethyl) trimethylsilylane, diazomethyltrimethyl silane, and Nysted's reagent or a precursor of the methylenating agent selected from freshly powdered triphenylmethyl phosphinium iodide, triphenylmethyl phosphinium bromide and triphenylmethyl phosphinium chloride, at a temperature from −78 to 110° C. in an organic solvent; and the compound of formula (IV) is prepared in a process step B by reacting a compound of formula (II) with formoxime:

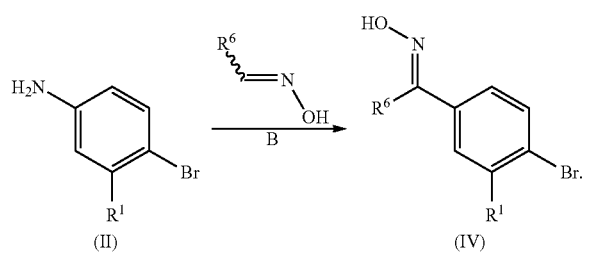

2. The process according to claim 1, wherein in step A.2 a precursor of the methylenating agent is used, said precursor is selected from freshly powdered triphenylmethyl phosphonium iodide, triphenylmethyl phosphonium bromide or triphenylmethyl phosphonium chloride and which is activated by the addition of a base.

3. The process according to claim 2, wherein the precursor of the methylenating agent used is triphenylmethyl phosphonium bromide or triphenylmethyl phosphonium chloride.

4. The process according to claim 1, wherein the base is selected from a group consisting of an alkali metal alcoholate, an organolithium reagent, and lithium or sodium amide.

5. The process according to claim 4, wherein the base is an alkali metal alcoholate.

6. The process according to claim 5, wherein the base is potassium methoxide or sodium methoxide.

7. The process according to claim 1, wherein the reaction of step A.2 is carried out in an aromatic hydrocarbon or a cyclic or an acyclic ether.

8. The process according to claim 1, wherein the reaction of step A.2 is carried out in benzene, toluene, xylenes, cumene, chlorobenzene, dichlorobenzenes, nitrobenzene, pyridine, tert-butylbenzene, diethyl ether, tert-butyl methyl ether (MTBE), cyclopentyl methyl ether, tetrahydrofuran (THF), methyl THF or dioxane.

9. The process according to claim 7, wherein the reaction is carried out in diethyl ether or THF.

10. The process according to claim 1, wherein in step A.2 the precursor phosphonium salt, the compound of formula (VII) and the solvent are placed in the reaction vessel, and the base is added subsequently in solid form or as solution to this mixture.

11. The process according to claim 10, wherein after completion of the reaction, the solvent is distilled off and a non-polar solvent is added.

12. The process according to claim 11, wherein with the addition of the non-polar solvent, the triphenylphosphine oxide is precipitated and filtered off.

13. The process according to claim 10, wherein the compound of formula (VIII) is distilled from the non-polar solvent solution.

14. The process according to claim 13, wherein the compound of formula (VIII) is worked-up under non-aqueous conditions.

15. The process according to claim 1, wherein in an upstream process step A.1, the compound of formula (VII) is obtained by reacting a compound of the formula (VI) with Magnesium or a Grignard reagent and with a di- or trifluoroacetic acid derivative

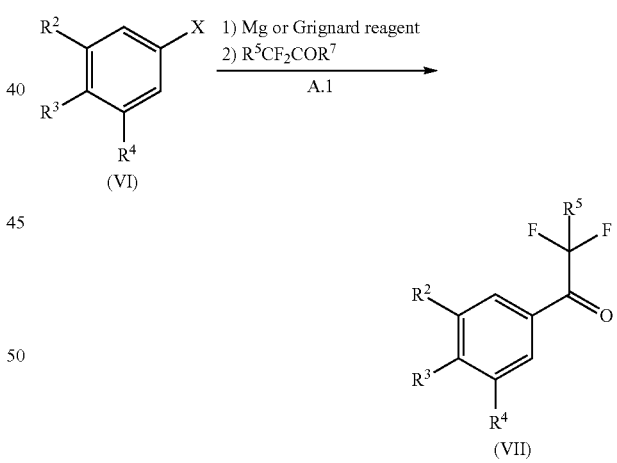

wherein,
R² to R⁵ are defined as in claim 1;
R⁷ is selected from the group consisting of OH, $F_3CCOO$, halogen, $C_1$-$C_6$-alkoxy, $N(CH_3)_2$, $N(C_2H_5)_2$, $N(OCH_3)CH_3$, piperidine, morpholine and piperazine, and wherein the last three radicals are bound via their nitrogen atom;
X is halogen;
Mg is Magnesium in form of turnings or powder; and the Grignard reagent is a $C_1$-$C_4$-alkyl magnesium halogenide.
16. The process according to claim 15, wherein X of formula (VI) is chloro or bromo.

17. The process according to claim 15, wherein process stage A.3 is splitted in a first step A.3a, wherein compound of formula (IV) first reacts with the chlorinating agent to an intermediate compound of formula (V)

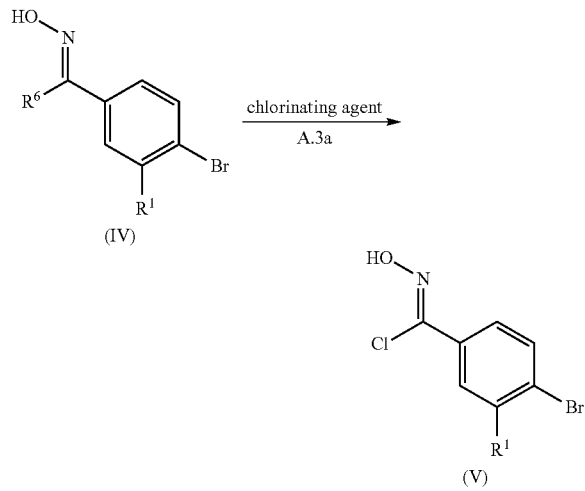

and then
in a second step A.3b, wherein the compound of formula (V) is reacted with a compound of formula (VIII) to form a compound of the formula (XV) in presence of a base

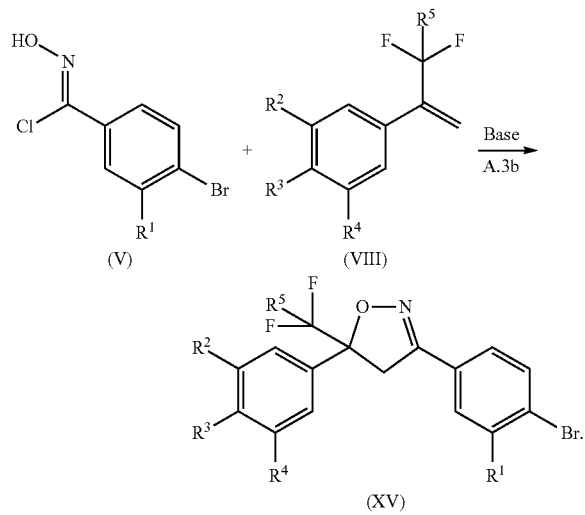

18. A process according to claim 17, wherein the base in step A.3 or A.3b is selected from a group consisting of triethylamine, pyridine, potassium carbonate, sodium carbonate, potassium hydrogen carbonate, sodium hydrogen carbonate, and ethyl magnesium bromide.

19. The process according to claim 1, wherein the pressure of the reaction of the compounds of the formula (XV) with carbon monoxide and an amine to a compound of formula (I) in step A.4 is in a range of 0.9 to 100 bar.

20. The process according to claim 19, wherein the pressure of the reaction of the compounds of the formula (XV) with carbon monoxide and an amine to a compound of formula (I) in step A.4 is in a range of 0.9 to 50 bar.

21. The process according to claim 1, wherein the pressure of the reaction of the compounds of the formula (XV) with carbon monoxide and an amine to a compound of formula (I) in step A.4 is in a range of 0.9 to 20 bar.

22. The process according to claim 1, wherein the process of step B is splitted in a first step B.1a, wherein a compound of the formula (II) is reacted with formoxime to compound of the formula (III)

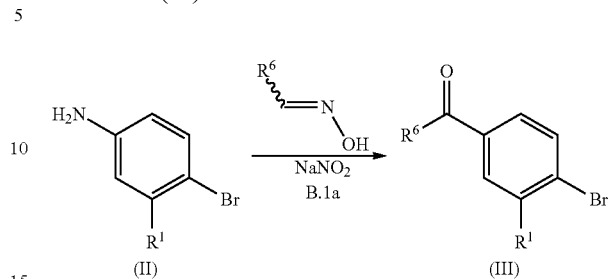

wherein $R^1$ and $R^6$ are defined as in claim 1;
and
in a second step B.1b, wherein the compound of formula (III) is further reacted with hydroxylamine to a compound of the formula (IV)

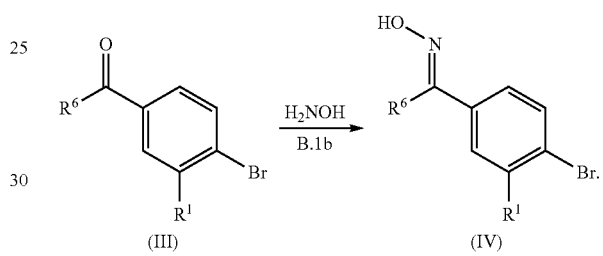

23. The process according to claim 22, wherein the compound of the formula (II) is provided in a further upstream process step C.1) by brominating a compound of formula (IX)

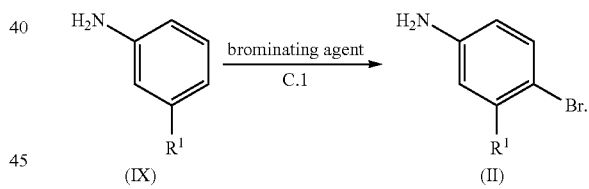

24. The process according to claim 23, wherein the brominating agent in C.1 is selected from the group consisting of bromine, N-bromsuccinimide, dibromo-dimethylhydantoine, aqueous $HBr/H_2O_2$, pyridinium hydrobromide, bromine pentafluoroantimonate hydrofluoride and the compound of the formula (XVII):

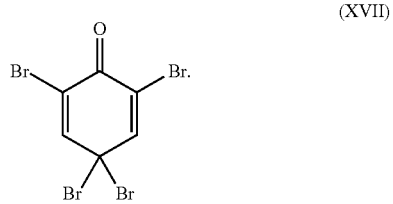 [SMILES: O=C1C(Br)=CC(Br)(Br)C=C1Br]

* * * * *